United States Patent [19]
Lloyd et al.

[11] Patent Number: 5,709,202
[45] Date of Patent: *Jan. 20, 1998

[54] INTRAPULMONARY DELIVERY OF AEROSOLIZED FORMULATIONS

[75] Inventors: Lester John Lloyd, Orinda; Peter M. Lloyd, Oakland; Reid M. Rubsamen, Berkeley, all of Calif.

[73] Assignee: Aradigm Corporation, Hayward, Calif.

[*] Notice: The term of this patent shall not extend beyond the expiration date of Pat. No. 5,544,646.

[21] Appl. No.: 65,660

[22] Filed: May 21, 1993

[51] Int. Cl.$^6$ ................................................ A61M 11/00
[52] U.S. Cl. .......................... 128/200.14; 128/200.23; 128/203.12; 128/204.23
[58] Field of Search .................... 128/200.14, 200.16, 128/200.19, 200.22, 203.12, 203.15, 203.21, 204.21, 204.23, 200.23

[56] References Cited

U.S. PATENT DOCUMENTS

| | | |
|---|---|---|
| 3,187,748 | 6/1965 | Mitchell et al. |
| 3,565,070 | 2/1971 | Hanson et al. |
| 3,658,059 | 4/1972 | Steil |

(List continued on next page.)

FOREIGN PATENT DOCUMENTS

| | | | |
|---|---|---|---|
| 0 186 280 | 10/1985 | European Pat. Off. | |
| A-0 432 992 A1 | 6/1991 | European Pat. Off. | |
| 81 21383 | 5/1983 | France | |
| 1518998 | 7/1978 | United Kingdom | |
| 2055046 | 2/1981 | United Kingdom | 128/200.19 |
| 2 104 393 | 11/1992 | United Kingdom | |
| 2 255 918 | 11/1992 | United Kingdom | |
| 2 256 805 | 12/1992 | United Kingdom | |
| WO 90/13327 | 11/1990 | WIPO | |
| WO 91/14468 | 10/1991 | WIPO | |
| WO 92/09322 | 6/1992 | WIPO | |
| WO 92/11050 | 7/1992 | WIPO | |
| WO 93/03785 | 3/1993 | WIPO | |

OTHER PUBLICATIONS

Byron, P.R., ed., *Respiratory Drug Delivery* CRC Press, Inc., Boca Raron, FL, (1990). A title page and table of contents is enclosed herewith.

Newman et al., "Deposition of pressurized aerosols in the human respiratory tract" *Thorax* (1981) 36:52–55.

Newman et al., "Deposition of pressurised aerosols in the lung using radio–labelled particles" *Thorax* (1980) 35:234.

(List continued on next page.)

*Primary Examiner*—Aaron J. Lewis
*Attorney, Agent, or Firm*—Karl Bozicevic; Bozicevic & Reed LLP

[57] ABSTRACT

Liquid, flowable formulations including aqueous formulations of a pharmaceutically active drug are packaged in individual dosage unit containers which containers are interconnected to form a cellular array designed to be integrated into a dispensing device capable of individually opening dosage unit containers and aerosolizing the contents through a nozzle for delivery to a patient. The cellular array is comprised of a plurality of containers with each container having an opening(s) thereon from which a drug-containing formulation may be aerosolized. The dispensing device is a hand-held, self-contained, portable device comprised of a means for removing covers from the containers and automatically dispensing the formulation from individual containers, preferably in response to a signal obtained as a result of measuring the inspiratory flow of a patient. The cellular array is loaded into the dispensing device to form a system which can be used in a method of delivering drugs to a patient via the intrapulmonary route. In a preferred embodiment each container includes an opening covered by a membrane having a plurality of pores therein wherein the pores have a diameter of about 0.5 microns to 50 microns and the dispensing device includes a vibrating device which creates a vibration frequency such that formulation forced through the pores is aerosolized to particles having a diameter of about 1 micron to 100 microns.

13 Claims, 7 Drawing Sheets

U.S. PATENT DOCUMENTS

| | | | |
|---|---|---|---|
| 3,812,854 | 5/1974 | Michaels et al. | |
| 3,814,297 | 6/1974 | Warren. | |
| 3,826,413 | 7/1974 | Warren. | |
| 3,861,386 | 1/1975 | Harris et al. | 128/200.16 |
| 3,991,304 | 11/1976 | Hillsman. | |
| 4,119,096 | 10/1978 | Drews | 128/200.16 |
| 4,294,407 | 10/1981 | Reichl et al. | 128/200.16 |
| 4,334,531 | 6/1982 | Reichl et al. | 128/200.16 |
| 4,361,401 | 11/1982 | Smith, Jr. et al. | 356/36 |
| 4,484,577 | 11/1984 | Sackner et al.. | |
| 4,592,348 | 6/1986 | Waters, IV et al.. | |
| 4,627,432 | 12/1986 | Newell et al. | 128/200.19 |
| 4,648,393 | 3/1987 | Landis et al.. | |
| 4,677,975 | 7/1987 | Edgar et al.. | |
| 4,790,305 | 12/1988 | Zoltan et al.. | |
| 4,803,978 | 2/1989 | Johnson, IV et al.. | |
| 4,852,582 | 8/1989 | Pell. | |
| 4,877,989 | 10/1989 | Drews et al. | 128/200.16 |
| 4,896,832 | 1/1990 | Howlett. | |
| 4,926,852 | 5/1990 | Zoltan et al. | 128/200.23 |
| 5,033,463 | 7/1991 | Cocozza | 128/203.21 |
| 5,134,993 | 8/1992 | van der Linden et al. | 128/200.16 |
| 5,152,456 | 10/1992 | Ross et al.. | |

OTHER PUBLICATIONS

Newman et al., "How should a pressurized β–adrenergic bronchodilator be inhaled?" *Eur. J. Respir. Dis.* (1981) 62:3–21.

Newman et al., "Deposition of pressurized suspension aerosols inhaled through extension devices[1-3]" *Am. Rev. Respir. Dis.* (1981) 124:317–320.

Baum, E.A., et al., "A novel breath actuated piezo electronic inhaler" 3M Healthcare Product Bulletin, 3M House, Morley Street Loughborough. Leic S LE11 1EP, England, 1 page total.

Costar® Life Science Filtration Catalog, "Nucleopore® Polycarbonate Membranes" (1992) p. 7.

INTRAPULMONARY DELIVERY OF AEROSOLIZED FORMULATIONS

FIELD OF THE INVENTION

This invention relates generally to methods of drug delivery, containers and systems used in the intrapulmonary delivery of drugs. More specifically, the invention relates to a method of controlled delivery of flowable, liquid formulations and to devices, cellular arrays and drug dosage units used to carry out the methods.

BACKGROUND OF THE INVENTION

The intrapulmonary delivery of pharmaceutically active drugs is accomplished by two distinct methodologies. In accordance with one method, a pharmaceutically active drug is dispersed in a low boiling point propellant (a CFC or HFC) and loaded in a pressurized canister from which the drug/propellant formulation may be released by the use of a device generally known as a metered dose inhaler (MDI). Once released, the propellant evaporates and particles of the drug are inhaled by the patient. The other method involve the use of a nebulizer which creates a mist of fine particles from a solution or suspension of a drug which mist is inhaled by the patient. Both methods are hindered by significant problems relating to patient compliance and dosing as described further below.

Metered dose inhalers that are generally manually operated and some breath actuated devices have been proposed and produced. Breath actuated inhalers typically contain a pressurized propellant and provide a metered dose automatically when the patient's inspiratory effort either moves a mechanical lever or the detected flow rises above a preset threshold, as detected by a hot wire anemometer. See, for example, U.S. Pat. Nos. 3,187,748; 3,565,070; 3,814,297; 3,826,413; 4,592,348; 4,648,393; 4,803,978; 4,896,832; and a product available from 3M Healthcare known as Aerosol Sheathed Actuator and Cap.

A major problem with manual metered dose inhalers is that the patient frequently actuates the device at the incorrect time during inspiratory flow to obtain the benefits of the intended drug therapy or during expiration. Thus, patients may inspire too little medication, or take a second dose and receive too much medication. The problem is, therefore, the inability to administer precise dosages.

One problem with breath activated drug delivery is that the dose is triggered on crossing a fixed threshold inspiratory effort. Thus, an inspiration efforts may be sufficient to release a metered dose, but the inspiratory flow following the release may not be sufficient to cause the aerosol medication to pass into the desired portion of the patient's airways. Another problem exists with patients whose inspiratory effort is not sufficient to rise above the threshold to trigger the release valve at all. Yet another problem is that the particle size can vary greatly and larger particles cannot enter the smaller lung passages and therefore are not delivered to the same degree and/or rate as are smaller particles. Any of these problems can make it difficult or impossible to monitor the delivery of a precise dosage of medication to a patient.

Attempts have been made to solve the patient inspiration synchronization problem. U.S. Pat. No. 4,484,577 refers to using a bidirectional reed whistle to indicate to the patient the maximum rate of inhalation for desired delivery of the drug and flow restrictor to prevent the patient from inhaling too rapidly. U.S. Pat. No. 3,991,304 refers to using biofeedback techniques to train the patient to adopt a desired breathing pattern. U.S. Pat. No. 4,677,975 refers to using audible signals and preselected time delays gated on the detection of inspiratory flow to indicate to the patient when to inspire and expire, and delivering inhalable material a selected time after the detected onset of flow. However, these devices also suffer from improper operation by patients who are not properly trained or do not conform their breathing to the instructed breathing pattern and whose inspiratory flow does not provide adequate delivery of the medication. Such problems make the delivery of predetermined dosages virtually impossible.

Studies in Byron (ed.), *Respiratory Drug Delivery*, CRC Press, Inc. (1990); Newman et al., *Thorax*, 1981, 36:52–55; Newman et al., *Thorax*, 1980, 35:234; Newman et al., *Eur. J. Respir. Dis.*, 1981, 62:3–21; and Newman et al., *Am. Rev. Respir. Dis.*, 1981, 124:317–320 indicate that during a single breath of an aerosol compound, only about ten percent of the total aerosol material presented is deposited into the lungs and that the location of deposition in the lung depends upon (1) breath parameters such as volume of inspiration, inspiratory flow rate, inspiratory pause prior to expiration, the lung volume at the time the bolus of medication is administered, and expiratory flow rate, (2) the size, shape and density of the aerosol particles (i.e., the medicinal compound, any carrier, and propellant), and (3) the physiological characteristics of the patient. Present devices and methods cannot eliminate these variables and as such cannot control dosage administration.

The publications authored by Newman et al. refer to measuring inspired air with a pneumotachograph to obtain a flow rate signal, which is integrated by a computer to determine lung capacity. A determined lung capacity, as a percent of vital capacity, is used as a threshold to actuate a solenoid to depress the canister of a manually actuated metered dose inhaler on the inspiration of the predetermined lung volume.

A problem with existing metered dose inhalers, whether or not breath actuated, is that they are factory preset to deliver a fixed dose at a given particle size distribution. Such devices are not capable of reducing the dose to reflect improvement in the patient's condition, or selecting a maximum desired respirable fraction of the aerosol mist that is suitable for a desired location of delivery of the medication in the particular patient.

Devices for controlling particle size of an aerosol are known. U.S. Pat. No. 4,790,305 refers to controlling the particle size of a metered dose of aerosol for delivery to the walls of small bronchi and bronchioles by filling a first chamber with medication and a second chamber with air such that all of the air is inhaled prior to the inhaling medication, and using flow control orifices to control the flow rate. U.S. Pat. No. 4,926,852 refers to metering a dose of medication into a flow-through chamber that has orifices to limit the flow rate to control particle size. U.S. Pat. No. 4,677,975 refers to a nebulizer device that uses baffles to remove from any aerosol particles above a selected size. U.S. Pat. No. 3,658,059 refers to a baffle that changes the size of an aperture in the passage of the suspension being inhaled to select the quantity and size of suspended particles delivered. A problem with these devices is that they process the aerosol after it is generated and thus are inefficient and wasteful.

It is well known that pulmonary functions, such as forced expiratory volume in one second, forced vital capacity, and peak expiratory flow rate, can be measured based on measured flow rates and used to (1) diagnose the existence of medical conditions, (2) prescribe medication, and (3) ascertain the efficiency of a drug therapy program. See, for example, U.S. Pat. Nos. 3,991,304 and 4,852,582 and the publications of Newman et al. discussed above. Heretofore, these tests have been performed using available spirometers. U.S. Pat. No. 4,852,582 also refers to using a peak flow rate meter to measure changes in peak flow rate before and after administration of a bronchodilator. The results of such tests before and after administration of several different medications are used to evaluate the efficiency of the medications.

A problem with the foregoing pulmonary function test devices is that they are too complicated for most patients to use effectively and obtain repeated delivery of a given amount of drug. Another problem is that the test data must be examined and interpreted by a trained medical practitioner to be meaningful. Another problem is that they do not provide adequately for altering the dosage of the medication administered in a single patient during the course of therapy, or from patient to patient, using the same delivery device for generating an aerosol of the same or different medications.

Attempts have been made to solve many of the above-referred-to problems. However, inconsistent user compliance combined with undesirably large particle size continues to cause problems with obtaining precise dosing.

Nebulizers utilize various means in order to create a fog or mist from an aqueous solution containing a pharmaceutically active drug. The mist created by the nebulizer device is directed towards the face of the patient and inhaled through the mouth and nose. Nebulizer devices and methodology can be quite useful when the precise dosing of the drug being delivered to the patient is not of particular importance. For example, in some situations the nebulizer creates a mist from an aqueous solution containing a bronchodilator which can be inhaled by the patient until the patient feels some improvement in lung function. When precise dosing is more important the nebulizer device and delivery methodology suffers from many of the disadvantages of metered dose inhaler devices and methodology as described above. In addition, nebulizers are large in size and not hand-held, easily transportable devices like MDIs. Accordingly, a nebulizer can only be used within a fixed location such as the patient's home, the doctor's office and/or hospital. However, a portable nebulizer is taught in published PCT application W092/11050 incorporated herein by reference. Drug formulations placed in nebulizers are generally diluted prior to delivery. The entire diluted formulation must generally be administered at a single dosing event in order to maintain the desired level of sterility and the nebulizer cleaned after use. The present invention endeavors to address and solve these problems.

SUMMARY OF THE INVENTION

Liquid, flowable formulations including aqueous formulations of a pharmaceutically active drug are packaged in individual dosage unit containers which containers are interconnected to form a cellular array designed to be integrated into a dispersing device capable of individually opening dosage unit containers and aerosolizing the contents through a nozzle for delivery to a patient. The cellular array is comprised of a plurality of containers with each container having an opening (and preferably a nozzle) thereon from which a drug-containing formulation may be aerosolized. Containers without individual nozzles have their openings positioned in a flow path line with a nozzle on the device. The containers are preferably interconnected on the cellular array by a connecting means which allows the dispensing device to successively move from a first container to a second after dispersing formulation from the first container and successively move to other containers as needed until the desired amount of drug has been dispersed, aerosolized and administered to the patient. The connecting means of the cellular array preferably includes indices thereon which can be read directly by the patient or with the aid of a dispensing device to provide information such as the number of containers used and the number of unused containers remaining on the cellular array. The dispensing device is a hand-held, self-contained, portable device comprised of a means for removing covers from the containers and automatically dispersing the formulation from individual containers, preferably in response to a signal obtained as a result of measuring the inspiratory flow of a patient. The cellular array is loaded into the dispensing device to form a system which can be used in a method of delivering drugs to a patient via the intrapulmonary route. In a preferred embodiment each container opening is covered by a porous membrane having a plurality of pores therein which pores have a diameter of about 0.5 microns to 50 microns and the dispensing device includes a vibrating device which creates a vibration frequency such that formulation forced through the openings is aerosolized to particles having a diameter of about 1 micron to 100 microns.

An object of the invention is to provide a cellular array comprised of a plurality of containers each with an opening or a nozzle thereon from which a liquid, flowable formulation in the container may be aerosolized.

Another object of the invention is to provide a dispensing device comprised of a means for forcing liquid flowable formulations from the nozzle of a container after a means for measuring the inspiratory flow of a patient determines a threshold flow and/or volume window was reached.

Another object is to provide a system for the intrapulmonary delivery of drug to a patient comprised of a cellular array loaded into a dispensing device designed to aerosolize drugs.

An advantage of the invention is that individual sterile containers, formulations and preferably nozzles are used for each administration of drug.

A feature of the invention is that drug can be aerosolized without the use of a low boiling point propellant and in particular without low boiling point fluorocarbons.

Another advantage of the invention is that the liquid drug solutions contained within the individual containers need not and do not include preservatives and/or any type of bacteriostatic compounds in that the containers are originally packaged as sterile, consists essentially of liquid drug alone or in combination with a liquid and excipient carrier and the contents of the individual containers are used completely upon opening.

Another feature of the present invention is that a wide range of different pharmaceutically active drugs (with an excipient carrier as needed to form a liquid formation) can be packaged within the individual sterile containers.

Another feature of the invention is that the individual containers of the cellular array preferably include a nozzle in the form a thin membrane having pores of substantially uniform diameter positioned thereon wherein the pores have a diameter in the range of about 0.5 microns to 50 microns.

Another feature of the invention is that the individual containers can be designed without nozzles but with openings which openings can be positioned in a flowable alignment with a nozzle positioned on the dispensing device.

Yet another feature of the present invention is that the dispensing device includes a vibrator or high frequency signal generation device which vibrates the device and/or liquid being dispensed from the device so as to create an aerosol having uniform particle size.

Another object of the invention is to provide a drug dispensing container comprised of two compartments and a nozzle wherein one compartment includes a pharmaceutically active drug and the second compartment interconnectable with the first includes a gas which can be used to aerosolize drug within the first compartment.

Another advantage of the present invention is that the system including the device and cellular array is a handheld, easily portable and usable device.

Another feature of the invention is that the cellular array may include indices thereon in the form of visually readable numbers or letters which can be readily perceived by the user whether a dose has been delivered for a particular day and/or time of day and/or indicate the number of doses on the array which have been used and the number which remain for use.

Still another feature of the invention is to provide a power source such as a battery in connection with indices on the cellular array which are in the form of magnetic, optical and/or electronic records which can be read by the drug dispensing device which in turn presents a visual display to the user providing information on the amounts and times of doses released and/or to be released.

It is another object of this invention to provide a pocket-sized, single, integrated device for recording the date, time and amount of aerosolized drug delivered at each drug delivery event which device is also capable of monitoring pulmonary function and maintaining a record of the date, time and value of each objective lung function and recording the information on a cellular array.

It is another object of this invention to provide a device capable of monitoring and recording objective pulmonary function information and displaying such information in a manner integrated with drug dosing event information so as to provide a means of evaluating quantitative, objective measures of pulmonary function in the context of actual administered therapy.

It is another object of this invention to show that the evaluation of pulmonary function in light of actual patient compliance only has meaning if drug dosing events are actually associated with patient inspiration and firing of the aerosolized drug into the patient's mouth.

It is another object of this invention to show that interpretation of pulmonary function data in the context of actual drug dosing events allows physicians to counsel patients accurately with regard to avoidance of overdosing of potentially toxic inhaled aerosolized drugs such as bronchodilators and gives physicians a tool for quantitatively advising patients regarding adjustments to their long-term, anti-inflammatory, aerosolized drug treatment program and/or long term enzyme treatment program.

These and other objects, advantages and features of the present invention will become apparent to those persons skilled in the art upon reading the present disclosure and reviewing the figures forming a part hereof wherein like numerals refer to like components.

DETAILED DESCRIPTION OF PREFERRED EMBODIMENTS

Figure 1:
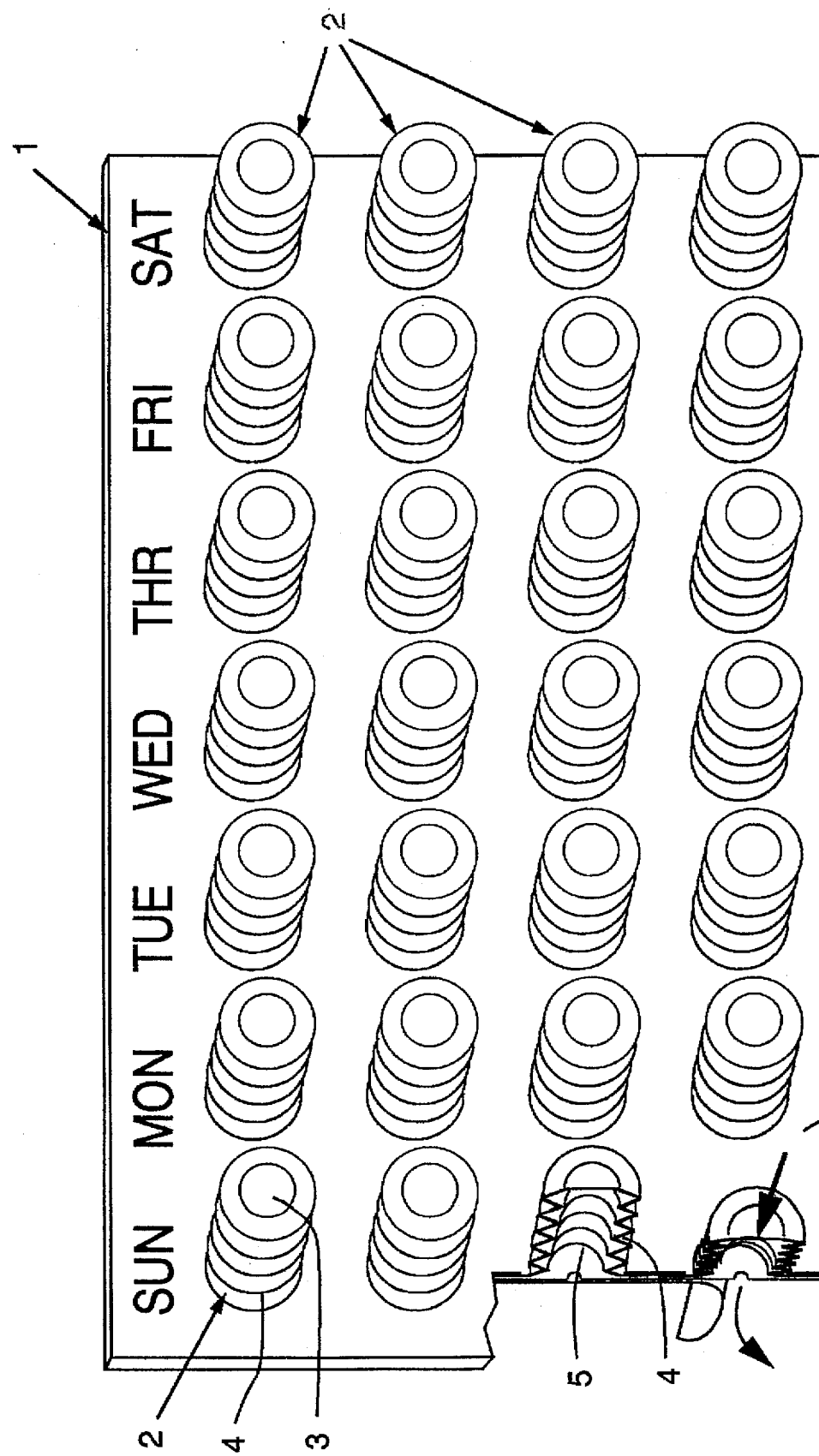
FIG. 1 is a perspective view of a cellular array of the present invention.

Before the devices, systems and methodology of the present invention are described, it is to be understood that this invention is not limited to the particular devices, systems, components, formulations and methodology described, as such may, of course, vary. It is also to be understood that the terminology used herein is with the purpose of describing particular embodiments only, and is not intended to limit the scope of the present invention which will be limited only by the appended claims.

It must be noted that as used herein and in the appended claims, the singular forms "a," "and," and "the" include plural referents unless the context clearly dictates otherwise. Thus, for example, reference to "a formulation" includes mixtures of different formulations and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited in connection with.

Definitions

The term "cellular array" shall be interpreted to mean two or more containers linked together by an interconnecting means wherein each of the containers includes its own individual opening or nozzle and each container includes at least one surface which is collapsible in a manner so as to allow the forced displacement of the contents of the container out of the opening or nozzle (without rupturing the container) in a manner such that the contents is aerosolized. The contents of each container preferably consists essentially of a liquid, flowable formulation which includes a pharmaceutically active drug and (if the drug is not liquid and of a sufficiently low viscosity to allow the drug to be aerosolized) an excipient carrier, i.e. preferably without any additional material such as preservatives which might affect the patient. The formulation is a liquid, flowable formulation with a relatively low viscosity that can be readily aerosolized and is more preferably a flowable, liquid formulation consisting essentially of a pharmaceutically active drug dissolved or dispersed in an excipient carrier. Preferred embodiments of cellular arrays have porous membranes covering openings which membranes act as nozzles. Further, each container on the array is preferably positioned in close proximity to one or more openings through which gas can be forced.

The term "dosing event" shall be interpreted to mean the administration of a pharmaceutically active drug to a patient in need thereof by the interpulmonary route of administration which event may encompass the release of drug contained within one or more containers on the cellular array. Accordingly, a dosing event may include the release of drug contained within a single container of the cellular array or the drug contained within a plurality of such containers when the containers are administered at about the same time (e.g., within 10 minutes of each other, preferably within 1–2 minutes of each other). A dosing event is not interrupted by a monitoring event which would indicate, if followed by further drug delivery, the beginning of a new dosing event.

The term "monitoring event" shall be interpreted to mean an event taking place prior to a "dosing event" whereby the inspiratory flow of the patient's inhalation is measured in order to determine the optimal cumulative volume and inspiratory flow at which to actuate the firing of a mechanism such as a roller or piston which causes the collapse of a container wall forcing the drug from the container in a manner such that the drug is aerosolized. It is preferable to carry out a "monitoring event" immediately prior to (within two minutes or less) each "dosing event" so as to optimize the ability to repeatedly deliver the same amount of drug to the patient at each dosing event.

The term "inspiratory flow" shall be interpreted to mean a value of air flow calculated based on the speed of the air passing a given point along with the volume of the air passing that point with the volume calculation being based on integration of the flow rate data and assuming atmospheric pressure and temperature in the range of about 18° C. to about 30° C.

The term "inspiratory flow profile" shall be interpreted to mean data calculated in one or more monitoring events measuring inspiratory flow and cumulative volume, which profile can be used to determine a point within a patient's inspiratory cycle which is optimal of the release of drug from a drug container on a cellular array to be delivered to a patient. It is emphasized that the optimal point within the inspiratory cycle for the release of drug is not calculated based on a point within the cycle likely to result in the maximum delivery of drug but rather a point in the cycle most likely to result in the delivery of the same amount of drug to the patient at each release of drug.

The term "respiratory drug" shall be interpreted to mean any pharmaceutically effective compound used in the treatment of any respiratory disease and in particular the treatment of diseases such as asthma, bronchitis, emphysema and cystic fibrosis. Useful "respiratory drugs" include those which are listed within the Physician's Desk Reference. Such drugs include beta adrenergics which include bronchodilators including albuterol, isoproterenol sulfate, metaproterenol sulfate, terbutaline sulfate, pirbuterol acetate and salmeterol. Anti-inflammatory drugs used in connection with the treatment of respiratory diseases include steroids such as beclamethasone dipropionate, triamcinolone acetonide and flunisolide. Other anti-inflammatory drugs include cromoglycates such as cromolyn sodium. Other respiratory drugs which would qualify as bronchodilators include anticholenergics including ipratropiumbromide. The present invention is intended to encompass the free acids, free bases, salts and various hydrate forms including semihydrate forms of such respiratory drugs and is particularly directed towards pharmaceutically acceptable formulations of such drugs which are formulated in combination with pharmaceutically acceptable excipient materials generally known to those skilled in the art and without other additives such as preservatives. Preferred drug formulations do not include additional components which have a significant effect on the overall formulation such as preservatives. Thus preferred formulations consist essentially of pharmaceutically active drug and a pharmaceutically acceptable carrier. However, if a drug is liquid without an excipient the formulation may consist essentially of the drug which has a sufficiently low viscosity that it can be aerosolized using a dispenser of the present invention.

The terms "formulation" and "liquid formulation" and the like are used interchangeably herein to describe any pharmaceutically active drug by its or with a pharmaceutically acceptable carrier in flowable liquid form. Such formulations are preferably solutions, e.g. aqueous solutions, ethanolic solutions, aqueous/ethanolic solutions, saline solutions and colloidal suspensions.

The terms "lung function" and "pulmonary function" are used interchangeably and shall be interpreted to mean physically measurable operations of a lung including but not limited to (1) inspiratory and (2) expiratory flow rates as well as (3) total lung volume. Methods of quantitatively determining pulmonary function are used to measure lung function. Quantitative determination of pulmonary function is important because lung disease is typically associated with deteriorating pulmonary function. Methods of measuring pulmonary function most commonly employed in clinical practice involve timed measurement of inspiratory and expiratory maneuvers to measure specific parameters. For example, forced vital capacity (FVC) measures the total volume in liters exhaled by a patient forcefully from a deep initial inspiration. This parameter, when evaluated in conjunction with the forced expired volume in one second ($FE_1$), allows bronchoconstriction to be quantitatively evaluated. A problem with forced vital capacity determination is that the forced vital capacity maneuver (i.e. forced exhalation from maximum inspiration to maximum expiration) is largely technique dependent. In other words, a given patient may produce different FVC values during a sequence of consecutive FVC maneuvers. The FEF 25–75 or forced expiratory flow determined over the mid-portion of a forced exhalation maneuver tends to be less technique dependent than the FVC. Similarly, the $FEV_1$ tends to be less technique dependent than FVC. In addition to measuring volumes of exhaled air as indices of pulmonary function, the flow in liters per minute measured over differing portions of the expiratory cycle can be useful in determining the status of a patient's pulmonary function. In particular, the peak expiratory flow, taken as the highest air flow rate in liters per minute during a forced maximal exhalation, is well correlated with overall pulmonary function in a patient with asthma and other respiratory diseases. The present invention carries out treatment by administering drug in a drug delivery event and monitoring lung function in a monitoring event. A series of events are carried out over time to determine if lung function is improved.

Each of the parameters discussed above is measured during quantitative spirometry. A patient's individual performance can be compared against his personal best data, individual indices can be compared with each other for an individual patient (e.g. $FEV_1$ divided by FVC, producing a dimensionless index useful in assessing the severity of acute asthma symptoms), or each of these indices can be compared against an expected value. Expected values for indices derived from quantitative spirometry are calculated as a function of the patient's sex, height, weight and age. For instance, standards exist for the calculation of expected indices and these are frequently reported along with the actual parameters derived for an individual patient during a monitoring event such as a quantitative spirometry test.

The term "respiratory disease" shall be interpreted to mean any pulmonary disease or impairment of lung function. Such diseases include restrictive and obstructive disease and diseases such as emphysema which involve abnormal distension of the lung frequently accompanied by impairment of heart action. Restrictive diseases tend to limit the total volume of air that a patient is able to exchange through inspiration and expiration. Restrictive disease, such as can be present in certain types of fibrotic processes, can therefore be detected by reduced FVC indices. Obstructive disease, such as is present in patients with asthma, tends not to affect the total volume of air exchangeable through inspiration and expiration but rather the amount of time required for forced exhalation of air. In particular, the $FEV_1$ is markedly reduced in patients with acute asthma symptoms. More specifically, the $FEV_1$, when taken as a ratio of FVC (i.e. $FEV_1$ divided by FVC), is markedly reduced in patients with acute asthma. In addition to increasing the amount of time required for a full forced expiration, the presence of acute bronchoconstrictive disease tends to decrease the peak expiratory flow measured over a typical forced exhalation.

The term "nozzle" shall be interpreted to mean any opening or group of openings which alone or in combination with other component(s) is capable of aerosolizing a fluid when a fluid is forced through the opening or group of openings. In preferred embodiments of the present invention the nozzle is present as one or more openings on a sealed container which holds a flowable liquid. However, the present invention can also be designed so that the container includes merely an opening or plurality of openings which functions in combination with a nozzle or nozzle components positioned on the dispensing device. The nozzle may be a system which includes openings on the container which openings are designed to operate in combination with additional component(s) positioned on the dispensing device which allow for the fluid to be aerosolized. In general, a nozzle or nozzle system includes any mechanism capable of converting the work of forcing the fluid from the container into kinetic energy in a manner which causes the flowable liquid to be aerosolized. In accordance with one preferred embodiment of the invention the containers on the cellular array include an opening covered by a membrane having a plurality of small openings or pores therein through which the liquid can be forced. A vibrating device is provided in the drug dispensing device which operates while liquid is forced through the openings on the container. Each container is preferably positioned in close proximity to an opening through which gas can be forced. Accordingly, the "nozzle" includes a system comprised of an opening on the container pores in the membrane covering the opening and opening(s) near the container along with the vibrating device which makes it possible to break up any stream of liquid forced through the pores so as to break the stream(s) into droplets and thereby aerosolize the liquid as the liquid is forced through the pores and inhaled by the patient. The openings positioned near the container opening aid in keeping particles from colliding with each other due to the gas forced through them which forms a stream of air which carries the particles along.

General Description

The present invention provides a non-invasive means of delivering any type of drug to a patient by the interpulmonary route. The devices and methodology used do not require the release of low boiling point propellants in order to aerosolize drug which propellants are conventionally used in connection with hand-held metered dose inhalers. However, like conventional hand-held metered dose inhalers the devices of the present invention are hand-held, self-contained, highly portable devices which provide a convenient means of delivering drugs to a patient via the intrapulmonary route. The liquid, flowable formulations of the present invention may include preservatives or bacteriostatic type compounds. However, the formulation preferably consists essentially of pharmaceutically active drug and pharmaceutically acceptable carrier. The formulation may consist essentially of the drug if the drug is freely flowable and can be aerosolized. Useful formulations may consist essentially of formulations currently approved for use with nebulizers. However, nebulizer formulations must, in general, be diluted prior to administration. The formulations are sterilized and packaged in individual containers in a sterile environment. Further, since preferred embodiments of the devices used in connection with the present invention include a means of analyzing breath flow and a microprocessor capable of making calculations based on the inhalation profile, the present invention can provide a means for repeatedly (1) dispensing and (2) delivering the same amount of drug to a patient at each dosing event.

The present invention includes at least four distinct aspects which include (1) a drug dosage unit, (2) a cellular array, (3) a drug dispensing device, and (4) a method of drug delivery.

The cellular array is comprised of two or more containers with each container having an opening(s) or, more preferably a nozzle positioned thereon. A preferred container includes an opening covered by a porous membrane. At least one wall of each container is collapsible in a manner so as to cause liquid present in the container to be forced out of the container through the opening or nozzle and be aerosolized. An interconnecting means connects each container with another. A preferred interconnecting means includes one or more openings thereon (in close proximity to each container) through which air may be forced so as to aid in preventing the collision of particles. The container is designed to include a pharmaceutically active drug in a liquid, flowable form. The drug formulation is preferably in a low viscosity liquid formulation which is most preferably a formulation which can be aerosolized easily and includes a respiratory drug. The viscosity of the drug by itself or in combination with a carrier must be sufficiently low that the aerosol can be formed which aerosol preferably has a particle size in the range of about one to 100 microns.

The interconnecting means is designed so that the cellular array can be readily integrated with and moved through a drug dispensing device. The cellular array preferably further includes openings through which a gas can be forced and indices which are positioned on individual containers or the interconnecting means. The indices may be connected to a power source such as a battery when the indices are in the form of visually perceivable numbers, letters or any type of symbol capable of conveying information to the patient using the device. Alternatively, the indices may be connected to a power source such as a battery when the indices are in the form of magnetically, optically or electronically recorded information which can be read by the drug dispensing device which in turn provides visual or audio information to the user. The indices can be designed for any desired purpose but in general provides specific information relating to the day and/or time which the drug within a container should be administered to the patient. Such indices may record, store and transfer information to the dispensing device regarding the number of containers on the cellular array, the number of containers used and/or the specific drug and amount of drug present in each container.

The containers on the cellular array are also referred to as drug dosage units. Each container includes at least one wall which can be collapsed to allow liquid contents present in the container to be forced out of an opening or nozzle of the container. In accordance with one embodiment the container has cylindrical walls with bellows or accordion-like undulations so that the bottom of the container can be forced upward towards the top of the container and allow liquid present within the container to be forced out of a plurality of pores in a membrane. The openings or pores are randomly spaced and have a diameter of from about 0.5 microns to about 50 microns and a pore density of about $1 \times 10^5$ to about $1 \times 10^8$ pores/cm$^2$. The membrane generally has a density of 0.5 to 2.0 mg/cm$^2$, more preferably about 1.0 mg/cm$^2$ and a thickness of about 2 to about 20 µm (microns), more preferably about 8 to 12 µm (microns). The pores are generally positioned on the upper portion of the drug dosage unit and randomly positioned on a membrane such as a polycarbonate membrane. The membrane material may be hydrophilic or, more preferably, hydrophobic. Nozzles or membranes of the invention may be produced using the same techniques used to produce microfilters, e.g. electro forming in nickel. The membrane may have holes formed therein by anisotropic etching through a thin film semiconductor wafer comprised of silicon or germanium. Membranes and nozzles comprised of various types of polymeric material may also be used. When such a drug dosage unit is used it is necessary to vibrate the drug dosage unit and/or its contents to create sized particles from a stream as the liquid is forced through the pores and thereby aerosolized.

Containers of the cellular array may include two separate compartments with a first compartment containing the liquid, flowable drug or drug formulation and a second compartment containing gas which is preferably in a pressurized form. The first and second compartments are separate but are, at least in part, separated by a weakened wall or wall portion which can be ruptured upon the application of additional pressure such as by increasing the pressure within the second compartment by approximately 50% or more. The increased pressure is obtained by directing a mechanical means such as a roller, piston or blast of pressurized air against a collapsible wall of the second compartment. The collapsible wall and the remainder of the container must have sufficient structural integrity to be maintained intact (not rupture) while the contents are forced out, generally by the application of about 20 to 200 psi.

A cellular array is used in combination with a drug dispensing device. The drug dispensing device includes a mechanical means such as a piston or mechanical roller or other suitable means for applying force against a collapsible wall of the container on the cellular array. By applying force against the collapsible wall the wall is collapsed while the container remains intact (i.e. does not leak its contents) and the liquid flowable formulation contained within the container is forced from an opening through an opening or a nozzle and aerosolized. The force or pressure imparts kinetic energy to the fluid as it is forced from the container. As particles form and are driven into the air they encounter frictional resistance which causes the particles to slow and then collide. To aid in preventing particle collisions, air is forced from one or more openings near the containers to keep particles moving in an air flow. The air flow and particle flow lines may be parallel or angled toward each other at an angle of up to 90°. For example, the air flow may be in a line outward toward the patient and the particles may be forced in to the air flow via a particle flow line at a right angle to the air flow line. Thus, the particles will be "blown" out to the patient by the air flow.

The drug dispensing device preferably includes some sort of holding means which makes it possible to securely position an individual container at a particular location where the mechanical means is fired and drug is forced from the container. For the convenience of the user it is desirable for the device to be able to move from one container to the next container on the cellular array. The device may be capable of moving a container into position while simultaneously removing a cover sheet from the container allowing access to the nozzle and/or opening. Further, the device is preferably capable of moving an expended or emptied container out of position. Although it is possible to manually position one container after another in the device it is preferable to design the drug delivery devices so as to continuously move one container into position while removing a cover sheet, allowing the contents of the container to be dispersed and thereafter moving that container out of position so as to position a new container with its cover sheet removed. Accordingly, the drug dispensing device preferably includes a transport means which is capable of holding and successively moving individual containers of the cellular array into position for release of the drug. The device preferably includes a system which makes it possible to vibrate a container, its contents and/or the openings on the container while the contents of the container is being forced out of the openings. As discussed further below, vibration, and vibration at a particular frequency, is an important factor in obtaining appropriate aerosolation of the liquid as it is forced from openings on a container. The relationship or ratio between pore diameter, the speed at which the fluid is forced from the container, and the frequency of vibration can be adjusted to obtain the desired particle size for the aerosol. Lastly, the device includes a housing which interconnects the transport means and mechanical means, holding means and vibration means, if present. The mechanical means may be driven by a variety of different power sources including a spring actuated mechanism which is loaded by the patient who compresses the spring prior to each actuation.

As indicated in the background of the invention, conventional metered dose inhalers and nebulizers suffer from a number of disadvantages. These disadvantages result in the inability to use these devices to repeatedly deliver the same amount of drug to a patient. In part, this results from the fact that users of such devices actuate the release of the drug by pushing a button which opens a valve causing drug to be released. Such methodology is not desirable because the patient will often actuate drug release at the wrong point within the inspiratory cycle. The drug dispensing device of the present invention preferably includes electronic and mechanical components which eliminate direct user actuation of drug release. More specifically, the device preferably includes a means for measuring inspiratory flow and sending an electrical signal as a result of the measurement and also preferably includes a microprocessor which is programmed to receive, process, analyze and store the electrical signal of the means for measuring flow and upon receipt of signal values within appropriate limits sending an actuation signal to the mechanical means which causes drug to be released from an opening of a container on the cellular array.

Creating Aerosols

In order for any aspects of the present invention to be utilized an aerosol must be created. If liquid present within a drug dosage unit is merely forced out of an opening to create a steady stream of liquid and/or a plurality of different streams of liquid the streams cannot be readily inhaled. Accordingly, the drug cannot effectively enter the lungs for interpulmonary delivery to have the desired effects. To create an aerosol the liquid must be broken into particles having a diameter which is sufficiently small such that the patient can inhale the particles. Although the particle size will vary depending on factors such as the particular type of formulation being aerosolized, in general, the particle size will be in the range of about one micron to about 100 microns. In order to obtain small particle sizes sufficient to aerosolize a formulation a number of different nozzles and/or nozzle systems can be utilized and the present invention is intended to encompass such aerosolizing systems.

Before describing the details regarding aerosolizing liquid compositions some of the general systems which can be used in connection with the present invention will be described. Firstly, a container such as the container 16 shown within FIG. 3 can include a nozzle 21 which includes impediments 22 which are designed in a manner so as to disperse the kinetic energy of liquid forced against the impediments so as to aerosolize the liquid. If a nozzle is not present on the containers the liquid may be forced through an opening such as the opening 10 shown in FIG. 2. After being forced through the opening 10 the liquid will contact a nozzle (not shown) positioned on the drug dispensing device which nozzle will aerosolize the stream of liquid forced from the opening 10.

Figure 7:
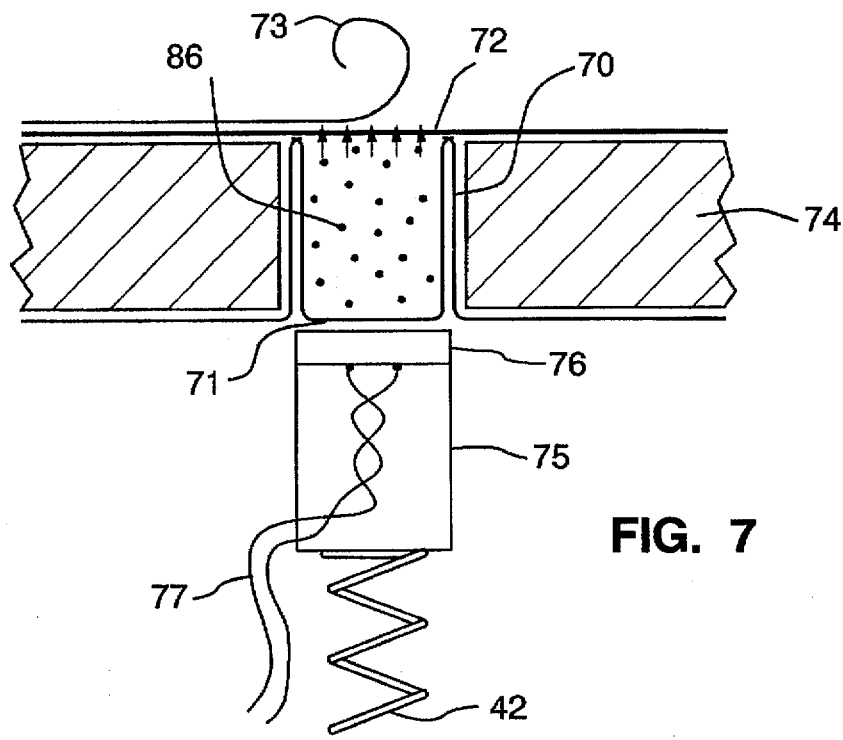
FIG. 7 is a cross-sectional plan view of another embodiment of a container of a cellular array positioned above a piston of a dispensing device.
Figure 8:
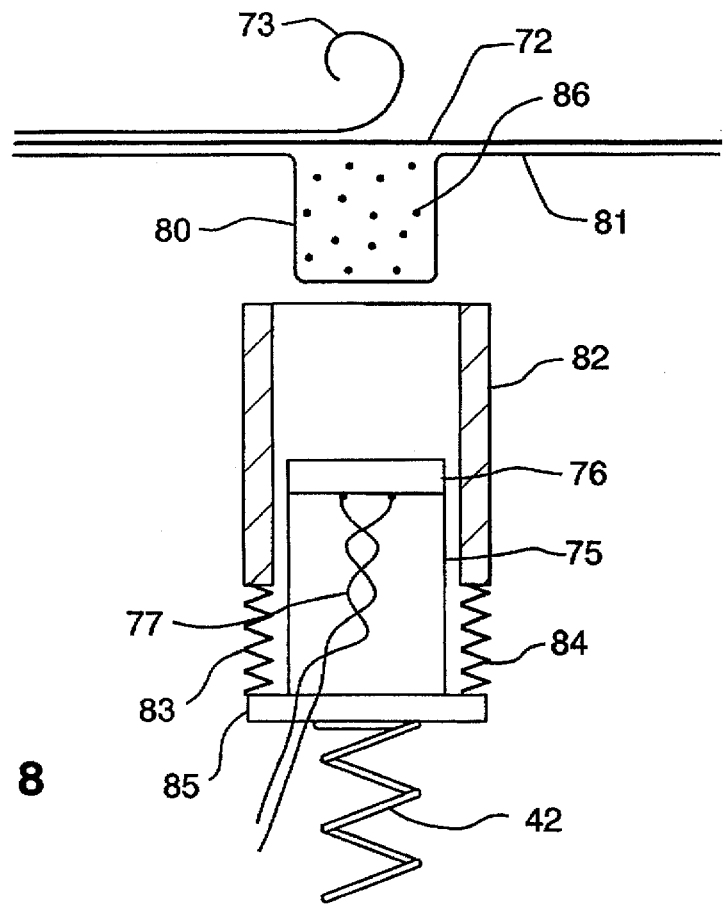
FIG. 8 is a cross-sectional plan view of another embodiment of a container of a cellular array positioned above a piston of a dispensing device.

More preferred embodiments of the present invention are shown in FIGS. 7 and 8 each of which includes a perforated polycarbonate membrane 72 having a plurality of openings positioned thereon. The liquid 86 in the containers are forced through the tiny openings in the polycarbonate membrane while the liquid, container and/or openings are simultaneously subjected to vibration. By vibrating at a particular frequency it is possible to form extremely small particles and create a fine mist aerosol. In that this is the preferred embodiment of the invention further details relating to such will be described further below.

In accordance with the preferred embodiments the liquid formulations present in the drug dosage units are aerosolized using an ultrasonic vibrator which vibrates the polycarbonate membrane 72 having a fixed porous structure. The particle size is determined by the size of the openings on the porous structure through which the liquid formulation is forced, the rate at which the fluid is forced from the container, and vibration frequency. More specifically, the aerosol particle size is a function of the diameter of the openings or pores through which the formulation is forced, vibration frequency, viscosity and liquid surface tension. In essence, the particle size diameter will be approximately twice the pore size diameter with a margin of error of approximately ±20%. For example, if the polycarbonate membrane used to cover the drug dosage unit includes pores having a diameter of 10 microns the aerosolized particles formed will have a size of approximately 18 to 22 microns in diameter. If the pore size of the polycarbonate membrane is approximately 4 microns in diameter the particles will have a diameter of about 7 to 9 microns in diameter. This relationship between particle size and pore diameter appears to hold over a pore sized diameter of approximately 0.5 microns to about 50 microns. Accordingly, it is possible to use membranes with pores therein having pore sizes of sufficient diameter to form aerosols having a particle sized diameter of about one micron to about 100 microns. Different types of membrane materials can be used in connection with the invention. In general, the membrane will have a density of about 0.5 to about 2.0 mg/cm$^2$, more preferably about 1.0 mg/cm$^2$ and a thickness in the range of from about 2 to about 20 μm, more preferably about 8 to 12 μm. The membrane will cover the entire opening of the container. The size and the shape of the opening can vary and will generally have an area in the range of about 0.25 cm$^2$ to about 10 cm$^2$ but more preferably about 1–2 cm$^2$.

A number of significant advantages can be obtained by using a cellular array which includes containers wherein the container openings are covered with the porous membrane of the present invention. Firstly, it is pointed out that such a cellular array provides a disposable nozzle in that the containers and the porous membranes are used only once, i.e. all drug in the container is preferably aerosolized in a single burst. By using the membranes only once, clogging of the pores is avoided or substantially reduced as compared to situations where a nozzle is used repeatedly. Further, a nozzle or aerosol creating the system of the type described herein provides relatively small particle sizes within a narrow particle size distribution. Accordingly, the smallest particles produced will not vary greatly in size as compared to the largest particles produced. More specifically, two-thirds or more of the particles produced will, preferably, have a particle size within 20% of the mean particle size. In that the preferred mean particle size is about 5 microns, the system will produce an aerosol wherein two-thirds or more of the particles within the aerosol have a particle size in the range of about 4 microns to about 6 microns. The system can aerosolize from about 50 μl to about 300 μl, more preferably, 200 μl of liquid from a single container. The contents of a container is generally aerosolized in a relatively short period of time, e.g., 1 second or less and inhaled by the patient in a single breath.

Drug dosage units of the present invention can be produced wherein the openings or pores are all uniform in size and are positioned at uniform distances from each other. However, the openings can be varied in size and randomly placed on the membrane. If the size of the openings is varied the size of the particles formed will also vary. In general, it is preferable to maintain uniform opening sizes in order to create uniform particle sizes and it is particularly preferable to have the opening sizes within the range of about 0.5 to about 5 microns which will create particle sizes of about one to 10 microns which are preferred with respect to inhalation applications. When the openings have a pore size in the range of 0.5 to 3 microns they will produce an aerosol having particle sizes in the range of 1 to 6 microns which is particularly useful for treating the bronchioli. Pore sizes having a diameter of about 3 to 5 microns will produce particle sizes having a diameter of about 6 to 10 microns which are particularly useful with respect to treating the bronchi.

In accordance with the present invention the drug dosage unit preferably includes pore sizes in the range of 0.5 microns to about 50 microns. Further, the pores are preferably separated, one from the other, in a random pattern providing about $1 \times 10^5$ to about $1 \times 10^8$ pores/cm$^2$. Further, the pore diameter indicates that at least 75% of the pores on the drug dosage unit fall within the prescribed range and preferably indicates that 85% or more of the pores fit within the prescribed range. Uniformity in pore size is desirable for creating uniformity in the particle size of the aerosol being delivered which is important with respect to maintaining consistency in dosing.

A variety of different types of materials can be used for performing the pore openings of the drug dosage units. It is important that the material which the pores are placed in has sufficient structural integrity such that when the liquid in the container is forced against the material the material will not break and the pore size will remain essentially constant under pressure. It has been found that porous ceramic oxides may be used as well as porous glasses, and metal frits, compressed porous plastics, and certain membranes including polycarbonate membranes including one preferred membrane referred to as "Nuclepore®" polycarbonate membranes produced by Costar Corporation which are commercially produced for use as filters to have a pore diameter in the range of 0.015 to 12 microns.

Although the thickness of the material on the drug dosage unit which includes the pore openings may be of any thickness, it is desirable for the material to be particularly thin e.g. less than one centimeter and more preferably less than one millimeter with particularly preferred components having a thickness in the range of about 0.1 millimeters to 0.005 millimeters. As the thickness of this material is increased the amount of energy necessary to force the liquid through the material is increased. Since the device of the present invention is a hand-held device it is important to produce materials which require the use of small amounts of energy in order to create the aerosol in that the energy supply is somewhat limited.

In most instances, a preferred aerosol dispersion will not be created merely by forcing a liquid against a porous membrane of the type described above. The porous membrane must be vibrated ultrasonically in order to produce an aerosol having the desired particle size. Such vibrations can be carried out by connecting an ultrasonic vibrator to the drug delivery device. The vibrator may be positioned on different components of the drug delivery device but is preferably positioned either near the pores of the membrane or within the piston or other means used to force the liquid from the drug dosage unit.

The ultrasonic vibrations can be obtained by the use of a piezoelictric ceramic crystal. The piezoelictric crystal is connected to a piston or the porous membrane by means of an atenuator horn or acoustic conduction mechanism, which when correctly matched with the piezoelectric crystal frequency, efficiently transmits ultrasonic oscillations of the piezoelectric crystal to the porous polycarbonate membrane and if sized correctly permits the ultrasonic energy to be focused in the polycarbonate membrane allowing for maximum use of the energy towards aerosolizing the liquid formulation. The size and shape of the atenuator horn is not of particular importance. It is preferred to maintain a relatively small size in that the device is hand held. The components are chosen based on the particular material used as the porous material, the particular formulation used and with consideration of the velocity of ultrasonic waves through the membrane to achieve a harmonic relationship at the frequency being used.

A high frequency signal generator drives the piezoelectric crystal. This generator is capable of producing a signal having a frequency of from about 1 kilohertz (Khz) to about 1,000 kilohertz. The power output required depends upon the amount of liquid being nebulized per unit of time and the area and porosity of the polycarbonate membrane used for producing the drug dosage unit and/or the efficiency of the connection. As a general rule, at least 2,000 dyne-cm are needed to nebulize one cubic centimeter of liquid into less than 20 micron particles. The best results are obtained when the power output is from about $1 \times 10^{10}$ to about $1 \times 10^{14}$ dyne-cm/sec.

The vibration is applied while the liquid is being forced from the pores of the polycarbonate membrane. The pressure required for forcing the liquid out can be varied depending on the liquid and the size of the pores but is generally in the range of about one to 200 psi, preferably 25 to 125 psi and may be achieved by using a piston, roller or a blast of forced compressed gas. The vibration frequency used and the pressure applied can be varied depending on the viscosity of the liquid being forced out and the diameter and length of the openings or pores. In general, the present invention does not create effective aerosols if the viscosity of the liquid is greater than about 500 centipoises.

When small aerosolized particles are forced into the air, the particles encounter substantial frictional resistance. This causes the particles to slow down quickly and may result in particles colliding into each other and combining, which is undesirable with respect to maintaining the preferred particle size distribution within the aerosol. In order to aid in avoiding the particle collision problem, it is preferable to include one or more openings in the cellular array in close proximity to the opening on the container. Air or any other gas is forced through these openings as the aerosol is forced from the container. Accordingly, an air flow is created toward the patient and away from the nozzle opening which carries the formed particles along and aids in preventing their collision with each other. The amount of gas forced from the openings will vary depending upon the amount of aerosol being formed. However, the amount of gas is generally five to one hundred times the volume of the liquid formulation within the container. Further, the flow rate of the gas is generally greater than the flow rate of the aerosolized particles being forced from the nozzle. The shape of the container opening, the shape of the membrane covering that opening, as well as the positioning and angling of the gas flow and particle flow can be designed to aid in preventing particle collision. When the two flow paths are substantially parallel, it is desirable to shape the opening and matching membrane so as to minimize the distance between any edge of the opening and the center of the opening. Accordingly, it is not desirable to form a circular opening which would maximize the distance between the outer edges of the circle and the center of the circle, whereas it is desirable to form an elongated narrow rectangle. Using such a configuration makes it possible to better utilize the air flow relative to all of the particles being forced from the container. When a circular opening is used, particles which are towards the center of the circle may not be carried along by the air being forced from the openings and will collide with each other. The elongated rectangle could be formed in a circle, thereby providing an annular opening and air could be forced outward from the outer and inner edges of the circle formed.

Cellular Array

Figure 3:
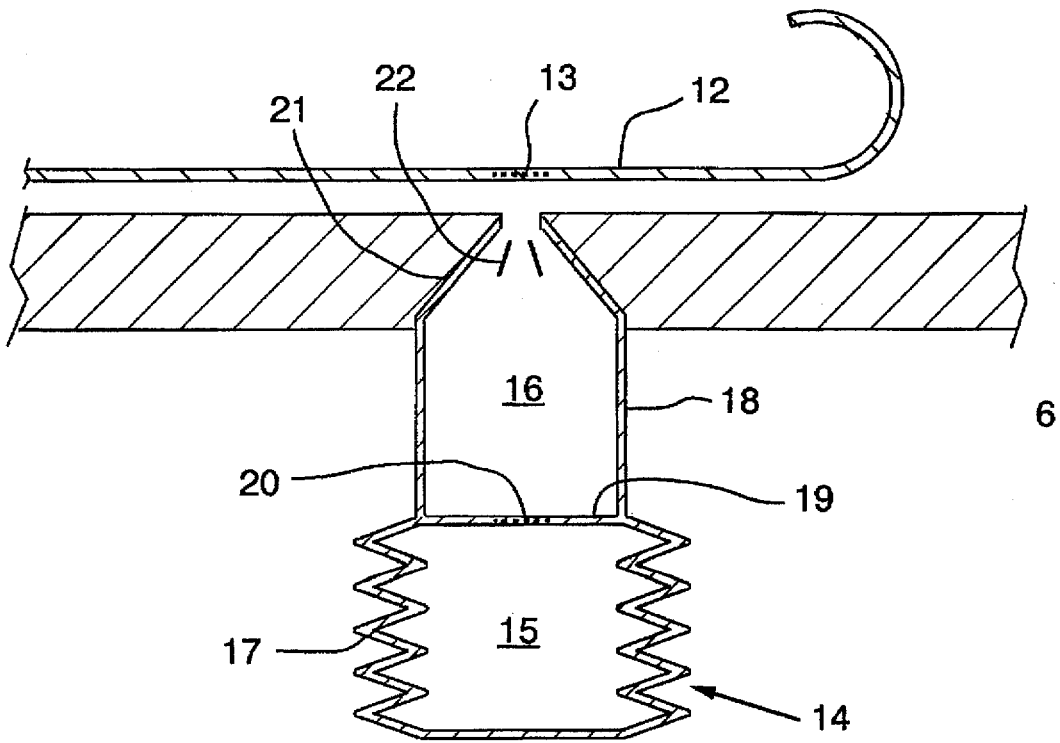
FIG. 3 is a cross-sectional view of a two compartment embodiment of a single dosage unit container of the invention.

FIG. 1 is a perspective view of a cellular array 1 of the present invention. The cellular array 1 is in the form of a rectangular card but it should be noted that the array can be in any desired shape including square, circular, oval, spiral in the shape of an elongated tape or other useful shapes designed for the particular dosage pattern of the particular patient. The array shown in FIG. 1 includes twenty-eight containers 2 positioned in four rows of seven. Each container 2 is comprised of a top surface 3, accordion or bellows shaped sidewalls 4 and an opening 5. The opening 5 may be part of a nozzle (as shown in FIG. 3) positioned on the container and extending outwardly from the other side of the cellular array. Each container 2 could be in a variety of different shapes and include more than one opening (such as the micro porous membrane of FIGS. 7 and 8). It is essential that the container be capable of holding a flowable, liquid formulation and that it include at least one surface which can be collapsed so as to force the formulation inside the container out of the opening(s) 5 while the remainder of the container remains intact, i.e. free of leaks and keeping the contents sterile.

The embodiment shown in FIG. 1 includes indices in the form of abbreviations for the days of the week which can be read by the user. If the user is to take the drug once a day then each container is labeled with a day of the week. However, if the user is to take the drug more than once a day such as four times a day then only one row of containers is labeled with the days of the week whereas the other rows within the column of four are labeled with different times of the day e.g. 6:00 a.m., 12:00 p.m., 6:00 p.m., 12:00 a.m. The labeling can be in any format and could include days of the month or other symbols or numbers in any variation or language.

In the embodiment as shown within FIG. 1 the containers 2 are interconnected by the interconnecting means 6 which is in the form of a rectangular card 6. Other interconnecting means are possible. For example, the containers can be interconnected by fusing one container to the next using one or more interconnecting lines. The card format shown in FIG. 1 is particularly convenient in that it allows for the indices to be written on the surface of the card adjacent to containers 2.

The card can provide a means for the placement of magnetic, optical and/or electronic indices. Such magnetic, optical or electronic indices cannot be read directly by the patient but are read by a reading mechanism in a drug dispensing device which reads and interprets the recorded signals and forwards the information to a microprocessor. The cellular array of FIG. 1 may include a power source such as a disposable battery which is attached to or embedded in the card 6. The power source could be used to maintain and operate an electronic memory. In addition, it could provide the power needed to operate the dispensing device. In such an embodiment, a new battery would be provided with each cellular array loaded into the dispensing device. Indices such as electronic indices could be placed on the surface of the containers 2 but are more preferably placed on the surface of the interconnecting means 6. In addition to disclosing specific information regarding the day and time for drug delivery the indices could provide more detailed information such as the amount of drug dispensed from each container which might be particularly useful if the containers included different amounts of drug. Further, magnetic, optical and/or electronic indices could have new information recorded onto them which information could be placed there by the drug dispensing device. For example, a magnetic recording means could receive information from the drug dispensing device indicating the precise time which the drug was actually administered to the patient. In addition to recording the time of delivery the device could monitor the expected efficacy of the delivery based on factors such as the inspiratory flow rate which occurred following the initial release of drug. The information recorded on the array could then be read by a separate device, interpreted by the caregiver and used to determine the usefulness of the present treatment methodology. For example, if the patient did not appear to be responding well but the recorded information indicating that the patient had taken the drug at the wrong time or that the patient had misdelivered drug by changing inspiratory flow rate after initial release it might be determined that further education in patient use of the device was needed but that the present dosing methodology might well be useful. However, if the recordings indicated that the patient had delivered the drug at the proper time using the proper techniques and still not obtained the correct results a different drug or dosing methodology might be recommended.

Other formats for the cellular array 1 as shown in FIG. 1 would include arrays with smaller numbers of containers thereon. For example, if the drug was to be delivered to the patient 2, 3 or 4 times a day the cellular array could be designed to include only 2, 3 or 4 containers (see FIG. 4). Thus the drug delivery device would be loaded with a new cellular array each day. If the drug was to be delivered once a day the array might include a strip of 7 containers so that the array could be loaded into the device on a once-a-week basis.

Figure 2:
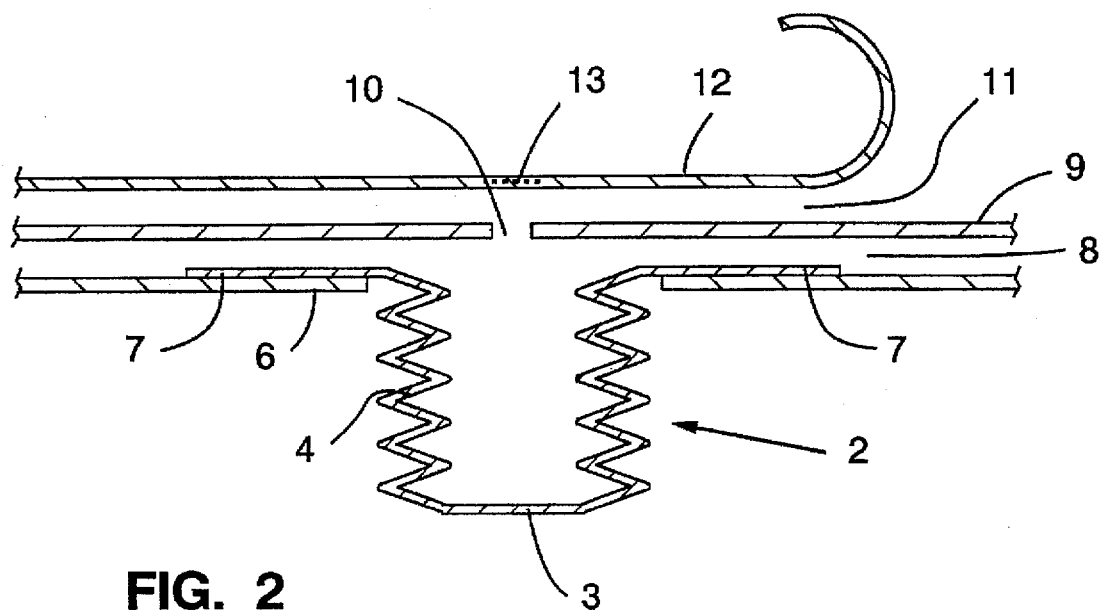
FIG. 2 is a cross-sectional view of a container of the invention.
Figure 9:
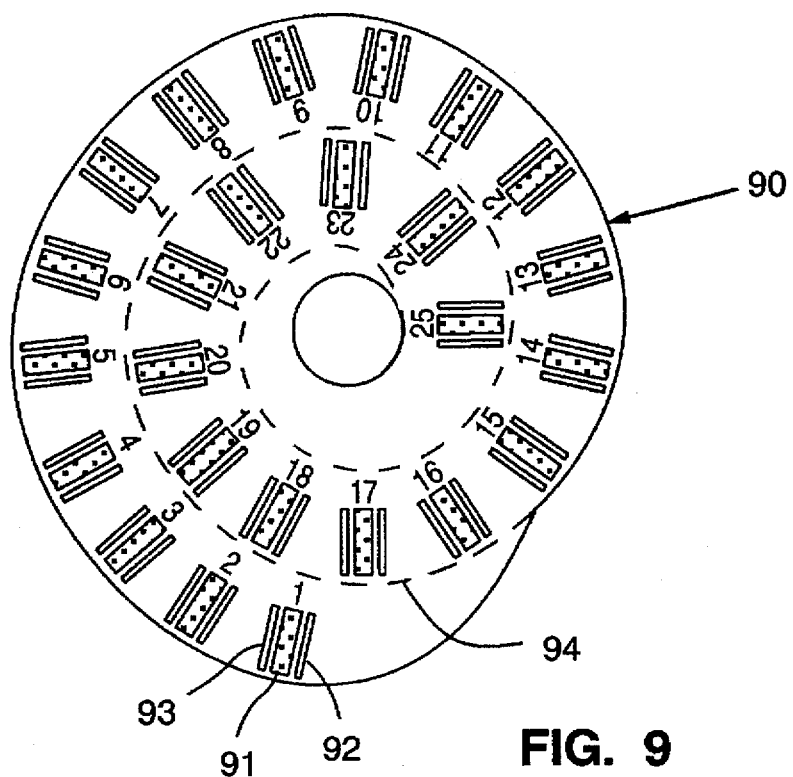
FIG. 9 is a top perspective view of a spiral configuration of containers on a cellular array.

FIG. 9 is a perspective view of a particularly preferred embodiment of a cellular array 90. The view of the array 90 shown in FIG. 9 is a top view showing openings 91. There are a total of 25 openings 91 shown and each of the openings 91 is in the form of an elongated rectangle marked by an indices 1–25. Each of the openings 21 is flanked on either side by openings 92 and 93. The openings 92 and 93 are not covered by a membrane as are each of the openings 91. The openings 92 and 93 are designed so as to allow air to flow freely outward in the direction of inspiratory flow path and may be parallel to or angled toward the flow of the particles being dispersed from the opening 91. The spiral configuration of the array 90 allows the array 90 to be loaded into a drug dispensing device which can move the array 90 from one container to the next in a continuous flow. The array 90 may include a perforation line 94 which makes it possible to easily tear the array 90 along the line 94 as the dispensing device moves from one container to the next.

It should be pointed out that the openings 91 are shown as elongated rectangles in FIG. 9. This is done in order to minimize the distance between any point within the opening 91 and the air flow which will be generated from the openings 92 and 93. Other configurations are also possible. For example, the elongated rectangular opening 91 could be bent into a circle so as to form an annular opening. The annular opening could be surrounded by openings on its outer perimeter and include an opening in its center through which air could be forced when aerosolized particles are being dispersed from a container. Further details regarding how the array 90 can operate within a drug dispensing device are described further below in connection with the description of FIG. 10.

Drug Dosage Unit

FIG. 2 shows a cross-sectional view of an individual container 2 showing the top 3 and shaped sidewalls 4 which are shown here as having an accordion or bellows shape which can fold in on itself to collapse. Preferred shapes include those which, like the bellows, make it possible to expel the contents of the container without stressing the container walls to a breakage point. In that the containers are to be designed to store their contents the container walls should be continuous i.e. a piston/cylinder design is not desirable in that contamination can occur over time. The embodiment shown in FIG. 2 is an embodiment which would, in general, be used in connection with another nozzle component (not shown) which component was positioned on the drug delivery device. The additional nozzle component is necessary in order to aerosolize the liquid being forced from the opening 10 in a generally continuous stream. The container 2 is embedded within the interconnecting means 6. Further, the accordion walls 4 of the container extend outwardly to provide an upper lid portion 7 which holds the container 2 in place on the card which is formed by the interconnecting means 6. Some type of securing means is used to secure the lip 7 to the surface of the card 6 such as an adhesive (which may be resealable) or bonding by heat. A layer of adhesive 8 is preferably included on the top surface of the lip 7 which adhesive 8 is used to secure a cover plate 9 in place above the container 2. The cover plate 9 includes an opening 10 which is preferably positioned over the center of the container 2. The cover plate 9 preferably includes a layer of resealable adhesive 11 on its upper surface which holds a removable cover sheet 12 in place. In order to dispense drug from the container 2 it is preferable to remove the cover sheet 12. However, the cover sheet 12 could be designed so that it includes a weakened portion 13 over the opening 10 which would be ruptured upon the application of pressure created by collapsing the container 2.

The container 2 can be in any desired size. In most cases the size of the container is not directly related to the amount of drug being delivered in that most formulations include relatively large amounts of excipient material e.g. water or a saline solution. Accordingly, a given size container could include a wide range of different doses by varying drug concentration. The amount of drug delivered to the patient will vary greatly depending on the particular drug being delivered. In accordance with the present invention it is possible to deliver a wide range of different drugs. For example, the drugs included within the container 2 could be drugs which have a systemic effect such as narcotic drugs delivered to provide relief from pain. However, in that the drugs are delivered directly to the lungs, respiratory drugs are preferred and include proteins such as Activase. The preferred respiratory drugs are albuterol, beclamethasone dipropionate, triamcinolone acetonide, flunisolide, cromolyn sodium, and ipratropium bromide, and include, free acids, bases, salts and various hydrate forms thereof generally administered to a patient in an amount in the range of about 100 µg–10,000 µg. These doses are based on the assumption that when interpulmonary delivery methodology is used the efficiency of the delivery is approximately 10% and adjustments in the amount released must be made in order to take into account the efficiency of the device. The differential between the amount of respiratory drug actually released from the device and the amount of respiratory drug actually delivered to the patient varies due to a number of factors. In general, the present device is approximately 20% efficient, however, the efficiency can be as low as 10% and as high as 50% meaning that as little as 10% of the released respiratory drug may actually reach the lungs of the patient and as much as 50% might be delivered. The efficiency of the delivery will vary somewhat from patient to patient and must be taken into account when programming the device for the release of respiratory drug. In general, a conventional metered dose inhaling device is about 10% efficient.

FIG. 3 shows a cross-sectional view of another embodiment of a container 14. The container 14 includes compartments 15 and 16. The compartment 15 is bound by flexible accordion shaped walls 17 whereas the compartment 16 includes cylindrical walls 18 which may be rigid or flexible. The compartment 15 includes a gas which is preferably pressurized. The gas in the container 15 is separated from container 16 by a wall 19 which includes a weakened portion 20 which can be ruptured by the application of additional pressure in the compartment 15. For example, if the pressure in the compartment 15 is increased to a level of 50% or more of the original pressure the weakened wall portion 20 will rupture allowing the gas within the compartment 15 to rush into the compartment 16. The compartment 16 holds the liquid, flowable formulation which include drug and if the drug is not flowable, a pharmaceutically acceptable excipient material.

The container 14 is also distinguishable from the container 2 shown in FIG. 2 in that the container 14 includes a nozzle 21 which nozzle includes impediments 22 which are designed so as to aerosolize the liquid flowable material forced out of the container 16. Those skilled in the art will contemplate other nozzle designs in reading this disclosure and such nozzles are intended as part of the present invention. As with the embodiment shown in FIG. 2 the opening of the nozzle is covered by a cover sheet 12 which can be removed by being peeled back as shown or alternatively can be ruptured at a weakened portion 13 positioned above the opening of the nozzle 21. The nozzle 21 as shown in FIG. 3 is distinguishable from the embodiment of FIG. 2 in that the nozzle 21 is capable of aerosolizing the liquid forced from the container 16 without the use of any further nozzle component positioned on the drug delivery device. However, it is possible to include such an additional component on the drug delivery device to provide for aerosolation of the liquid forced from the container 16.

It should be noted that the various components can be interchanged. For example, the container 2 shown within FIG. 2 can include a nozzle such as the nozzle 21 shown within FIG. 3. Alternatively, the container shown within FIG. 2 can include an additional compartment such as the compartment 15 shown within FIG. 3. A microporous membrane having microporous openings thereon of the type shown in connection with FIGS. 7 and 8 could also be used in connection with the embodiments shown in FIGS. 2 and 3. Such a microporous membrane would be particularly useful for use in connection with the embodiment of FIG. 2. The use of such a microporous membrane requires the use of a vibrating device as described further below in connection with FIGS. 7 and 8. Other variations will also be contemplated by those skilled in the art upon reading this disclosure. The important concepts which must be maintained are that the individual containers include doses of pharmaceutically active drug which are completely dispersed from the container and aerosolized in a single dispersion. This is done in order to avoid any contamination. Further, the individual containers are interconnected by an interconnecting means which can be fed to a drug dispensing device so that the containers can be successively emptied and delivered to a patient.

With respect to containers such as shown within FIG. 2 it is pointed out that some nozzle must be used in order to aerosolize the drug formulation being forced from the container. The nozzle can be included on the drug dispensing device or can be a movable nozzle which can be slid within a track positioned on the interconnecting means so that the nozzle is positioned above each opening 10 when the formulation within the container 2 is to be dispersed from that container. However, it is more preferable for each container to include its own individual nozzle in order to avoid any possible contamination problems i.e. maintain sterile conditions. Further, when a new nozzle is used with each container, there is no problem with residue build-up which can result in clogging. The most preferred nozzle is a system of components which includes the microporous membrane of the type shown in FIGS. 7 and 8 in combination with a vibrating device which is an energy-efficient means of producing a fine particle mist.

Figure 4:
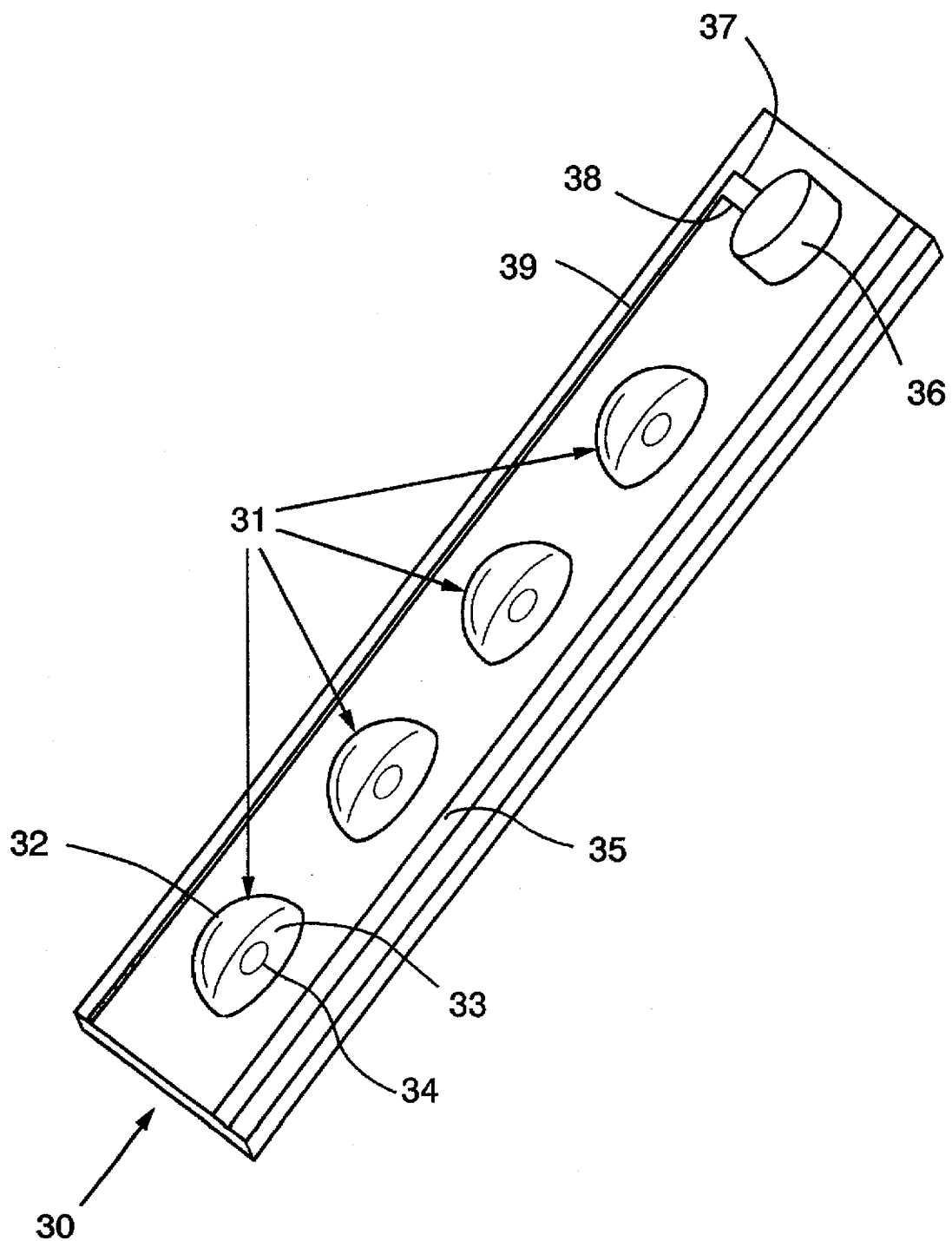
FIG. 4 is a perspective view of another embodiment of a cellular array of the present invention.

FIG. 4 is a perspective view of another embodiment of a cellular array 30. The cellular array 30 includes 4 compartments 31 positioned thereon. Each compartment 31 includes a bubble shaped top 32 which holds the pharmaceutical formulation therein. The bottom 33 of each compartment 31 includes an opening 34 through which the liquid formulation within the container can be forced when the top 32 is collapsed by the application of pressure. The array 30 shown in FIG. 4 is designed to include four doses which are delivered to a patient on a four-times-a-day basis thus the array 30 is loaded into the drug dispensing device on a once-a-day basis.

The array 30 of FIG. 4 shows a magnetic recording tape 35 positioned thereon. The tape 35 can have information recorded onto it by the drug dispensing device. The information can be later read by the caregiver to determine the effectiveness of treatment. A battery 37 may be included on or imbedded in the array 30. The battery is electrically connected by wires 37 and 38 or other electrical connectors to the strip 39. The strip 39 can contain, record and convey information to and from the drug dispensing device (of FIG. 6) and/or supply electrical power to the drug dispensing device. The battery 36 can also be connected to the strip 35 which can, in turn, be connected to the strip 39.

FIG. 7 is a cross sectional view of a portion of a cellular array positioned over a means for forcing the contents of the container outward. More specifically, FIG. 7 shows a cross section of a container 70 which includes cylindrical walls and a bottom collapsible wall 71. The top of the container is covered by a polycarbonate membrane 72 which can include openings having a diameter within the range of 0.5 microns to about 50 microns but more preferably includes openings having a diameter of about 1 micron to about 5 microns. The polycarbonate membrane 72 is covered by a cover film 73 and a removable adhesive is positioned between the membrane 72 and the cover film 73. However, the adhesive does not cover the openings covering the container 70, but rather the surrounding area, in that the adhesive could easily clog the small pores in the membrane 72 the adhesive surrounds but does not cover the area where formulation is forced out.

The embodiment shown in FIG. 7 shows a thick card portion 74. Thus the entire cellular array is substantially plainer on both of its surfaces. This is distinguishable from the cellular array as shown in cross section in FIG. 8. In accordance with the cellular array of FIG. 8 the containers 80 protrude outwardly from the surface of a card 81. Details regarding the operation of the drug dispensing system as a whole in connection with FIGS. 7 and 8 are described in the latter part of the section describing the operation of the drug delivery device.

Method of Administration

The method and device of the invention provides a number of features which make it possible to achieve the controlled and repeatable dosing procedure required for the treatment of diseases, particularly respiratory diseases such as asthma.

The method of the invention involves the release of a liquid, flowable drug from individual containers which may be interconnected on a cellular array. This is desirable in that the liquid, flowable drug is packaged under a sterile environment and therefore does not require and preferably does not include additional materials such as antifungal, bacteriostatics, and preservatives which would normally be required in a liquid formulation if the formulation was to be opened, exposed to air, closed and later used again. The present invention does not require the use of low boiling point propellants such as low boiling point fluorocarbons. The use of such low boiling point propellants in conventional metered dose inhaler devices is desirable because such propellants eliminate the need for preservatives, antifungal and bacteriostatic compounds. However, there are potential environmental risks to using low boiling point fluorocarbons. Accordingly, the present invention provides potential environmental benefits and would be particularly useful if government regulations prevented further use of devices which dispensed low boiling point fluorocarbons.

The method preferably uses a drug delivery device which is not directly actuated by the patient in the sense that no button is pushed nor valve released by the patient applying physical pressure. On the contrary, the device of the invention provides that the actuation mechanism which causes drug to be forced from a container is fired automatically upon receipt of a signal from a microprocessor programmed to send a signal based upon data received from a monitoring device such as an airflow rate monitoring device. A patient using the device withdraws air from a mouthpiece and the inspiratory rate, and calculated inspiratory volume of the patient is measured one or more times in a monitoring event which determines an optimal point in an inhalation cycle for the release of a dose of any desired drug. Inspiratory flow is preferably measured and recorded in one or more monitoring events for a given patient in order to develop an inspiratory flow profile for the patient. Recorded information is preferably analyzed by the microprocessor in order to deduce a preferred point within the patient's inspiratory cycle for the release of drug with the preferred point being calculated based on the most likely point to result in a reproducible delivery event.

A flow rate monitoring device continually sends information to the microprocessor, and when the microprocessor determines that the optimal point in the respiratory cycle is reached, the microprocessor actuates a component which fires a mechanical means (and, if present, vibration means) which causes drug to be forced out of the container and aerosolized. Accordingly, drug is always delivered at a pre-programmed place in the inspiratory flow profile of the particular patient which is selected specifically to maximize reproducibility of drug delivery and peripheral deposition of the drug. It is pointed out that the device of the present invention can be used to, and actually does, improve the efficiency of drug delivery. However, this is not the most important feature. A more important feature is the reproducibility of the release of a tightly controlled amount of drug at a particular point in the respiratory cycle so as to assure the delivery of a controlled and repeatable amount of drug to the lungs of each individual patient. Further, this is accomplished without the use of fluorocarbons and/or bacteriostatic compounds.

The combination of automatic control of the drug release mechanism, combined with frequent monitoring events in order to calculate the optimal flow rate and time for the release of respiratory drug, combine to provide a repeatable means of delivering respiratory drug to a patient. Because the drug release mechanism is fired automatically and not manually, it can be predictably and repeatedly fired at that same point in the inspiratory cycle. Because dosing events are preferably preceded by monitoring events, the point in the inspiratory cycle of the release can be readjusted based on the particular condition of the patient. For example, patients suffering from asthma have a certain degree of pulmonary insufficiency which may well change with the administration of drug. These changes will be taken into account in the monitoring event by the microprocessor which will readjust the point of release of the respiratory drug in a manner calculated to provide for the administration of an amount of respiratory drug to the patient presently needed by the patient at each dosing event.

When administering drug using the inhalation device of the present invention, the entire dosing event can involve the administration of anywhere from 10 µg to 1,000 mg, but more preferably involves the administration of approximately 50 µg to 10,000 µg. This amount of drug is in a liquid form or is dissolved or dispersed within a pharmaceutically acceptable, liquid, excipient material to provide a liquid, flowable formulation which can be readily aerosolized. The container will include the formulation having drug therein in an amount of about 50 µl to 300 µl, more preferably about 200 µl. The large variation in the amounts which might be delivered are due to different drug potencies and different delivery efficiencies for different devices. The entire dosing event may involve several inhalations by the patient with each of the inhalations being provided with drug from the device. For example, the device can be programmed so as to release the contents of a single container or to move from one container to the next on a cellular array of containers. Delivering smaller amounts from several containers can have advantages. Since only small amounts are delivered from each container and with each inhalation, even a complete failure to deliver drug with a given inhalation is not of great significance and will not seriously disturb the reproducibility of the dosing event. Further, since relatively small amounts are delivered with each inhalation, the patient can safely administer a few additional micrograms of drug (or milligrams for some drugs) without fear of overdosing.

In addition to drug potency and delivery efficiency, drug sensitivity must be taken into consideration. The present invention makes it possible to vary dosing over time if sensitivity changes and/or if user compliance and/or lung efficiency changes over time.

Based on the above, it will be understood that the dosing or amount of drug (and in particular respiratory drug) actually released from the device can be changed based on the most immediately prior monitoring event wherein the inspiratory flow of a patient's inhalation is measured.

Variations in doses are calculated by monitoring the effect of one or more lung function parameters in response to known amounts of respiratory drug released from each container and delivered to the patient. If the response in changing measured lung function parameters is greater than with previous readings, then the dosage (number of containers released) is decreased or the minimum dosing interval is increased. If the response in changing measured lung function parameters is less than with previous readings, then the dosing amount is increased or the minimum dosing interval is decreased. The increases and decreases are gradual and are preferably based on averages (of 10 or more readings of lung function parameter after 10 or more dosing events) and not a single dosing event and monitoring event. The preferred drug delivery device of the present invention can record dosing events and lung function parameters over time, calculate averages and deduce preferred changes in administration of respiratory drug.

One of the important features and advantages of the present invention is that the microprocessor can be programmed to take two different criteria into consideration with respect to dosing times. Specifically, the microprocessor can be programmed so as to include a minimum time interval between doses i.e. after a given delivery another dose cannot be delivered until a given period of time has passed. Secondly, the timing of the device can be programmed so that it is not possible to exceed the administration of a set maximum amount of drug within a given time. For example, the device could be programmed to prevent dispersing more than 200 µg (or two 100 µg containers of drug) of a particular drug within one hour. More importantly, the device can be programmed to take both criteria into consideration. Thus, the device can be programmed to include a minimum time interval between doses and a maximum amount of drug to be released within a given time period. For example, the microprocessor could be programmed to allow the release of a maximum of 200 µg of a given drug during an hour which could only be released in amounts of 25 µg with each release being separated by a minimum of five minutes.

The dosing program can be designed with some flexibility. For example, if the patient normally requires 250 µg per day of respiratory drug, the microprocessor of the inhalation device can be programmed to provide a warning after 250 µg have been administered within a given day and to continue the warning thereafter to alert the user of possible overdoses. By providing a warning and not a lock-out, the device would allow for the patient to administer additional respiratory drug, if needed, due to a decreased lung function and/or account for misdelivery of respiratory drug such as due to coughing or sneezing during an attempted delivery.

The ability to prevent overdosing is a characteristic of the device due to the ability of the device to monitor the amount of respiratory drug released and calculate the approximate amount of respiratory drug delivered to the patient based on monitoring a variety of lung function parameters. The ability of the present device to prevent overdosing is not merely a monitoring system which prevents further manual actuation of a button. As indicated above, the device used in connection with the present invention is not manually actuated, but is fired in response to an electrical signal received from a microprocessor (which received data from a monitoring device such as a device which monitors inspiratory flow) and allows the actuation of the device upon achieving an optimal point in a inspiratory cycle. When using the present invention, each actuation of the device will administer drug to the patient in that the device is fired in response to patient inhalation. More specifically, the preferred embodiment of the device does not allow for the release of respiratory drug merely by the manual actuation of a button to fire a burst of respiratory drug into the air or a container.

The microprocessor of the present invention preferably includes a timing device. The timing device can be electrically connected with visual display signals as well as audio alarm signals. Using the timing device, the microprocessor can be programmed so as to allow for a visual or audio signal to be sent when the patient would be normally expected to administer respiratory drug. In addition to indicating the time of administration (preferably by audio signal), the device can indicate the amount of respiratory drug which should be administered by providing a visual display. For example, the audio alarm could sound alerting the patient that respiratory drug should be administered. At the same time, the visual display could indicate "one dosage unit" as the amount of drug (number of containers) to be administered. At this point, a monitoring event could take place. After completion of the monitoring event, administration would proceed and the visual display would continually indicate the remaining amount of respiratory drug which should be administered. After the predetermined dose (indicated number of containers) had been administered, the visual display would indicate that the dosing event had ended. If the patient did not complete the dosing event by administering the stated amount of drug, the patient would be reminded of such by the initiation of another audio signal, followed by a visual display instructing the patient to continue administration.

Additional information regarding dosing with drugs can be found within Harrison's—Principles of Internal Medicine (most recent edition) and the Drug Evaluation Manual, 1993 (AMA—Division of Drugs and Toxicology), both of which are published by McGraw Hill Book Company, New York, incorporated herein by reference to disclose conventional information regarding dosing of drugs and in particular respiratory drugs as well as other useful drugs and formulations.

Supplemental Treatment Methodology

The present invention can be used to deliver all types of drugs. Specifically, the cellular arrays, drug dosage units and drug delivery systems can be used to deliver drugs which have a systemic effect (e.g., narcotics, proteins such as DNAse and antibiotics) as well as drugs which have a local effect primarily on the lungs (e.g., bronchodilators). Because the present invention allows drug delivery directly to the lungs there are certain advantages with respect to using the invention for the delivery of drugs to treat respiratory diseases. For this reason, much of the operation of the invention is described in connection with the delivery of respiratory drugs. However, the invention is not limited to respiratory drugs and the examples described herein would apply with respect to the delivery of drugs having a systemic effect. This is true also with respect to the supplemental treatment methodology described below even though this methodology is described with specific reference to respiratory diseases being treated with respiratory drugs.

Patients suffering from a given disease such as a respiratory disease may be treated solely with respiratory drug as indicated above, i.e. by intrapulmonary delivery. However, it is possible to treat such patients with a combination of intrapulmonary delivery and other means of administration such as oral administration. The oral drug is preferably given in amount so as to maintain a baseline level of drug within the circulatory system which is sufficient to maintain body functions such as lung function at an acceptable level. However, this baseline level of drug to blood ratio (or serum blood level) must be raised in order to improve the body function such as lung function during periods of stress such as respiratory difficulty such as an asthma attack and such can be accomplished by the interpulmonary administration of a drug such as a respiratory drug using the present invention.

Based on the above, it will be understood by those skilled in the art that a plurality of different treatments and means of administration can be used to treat a single patient. For example, a patient can be simultaneously treated with respiratory drug by transdermal administration, respiratory drug via intrapulmonary administration in accordance with the present invention, and drugs which are orally administered.

Drug Delivery Device

Figure 5:
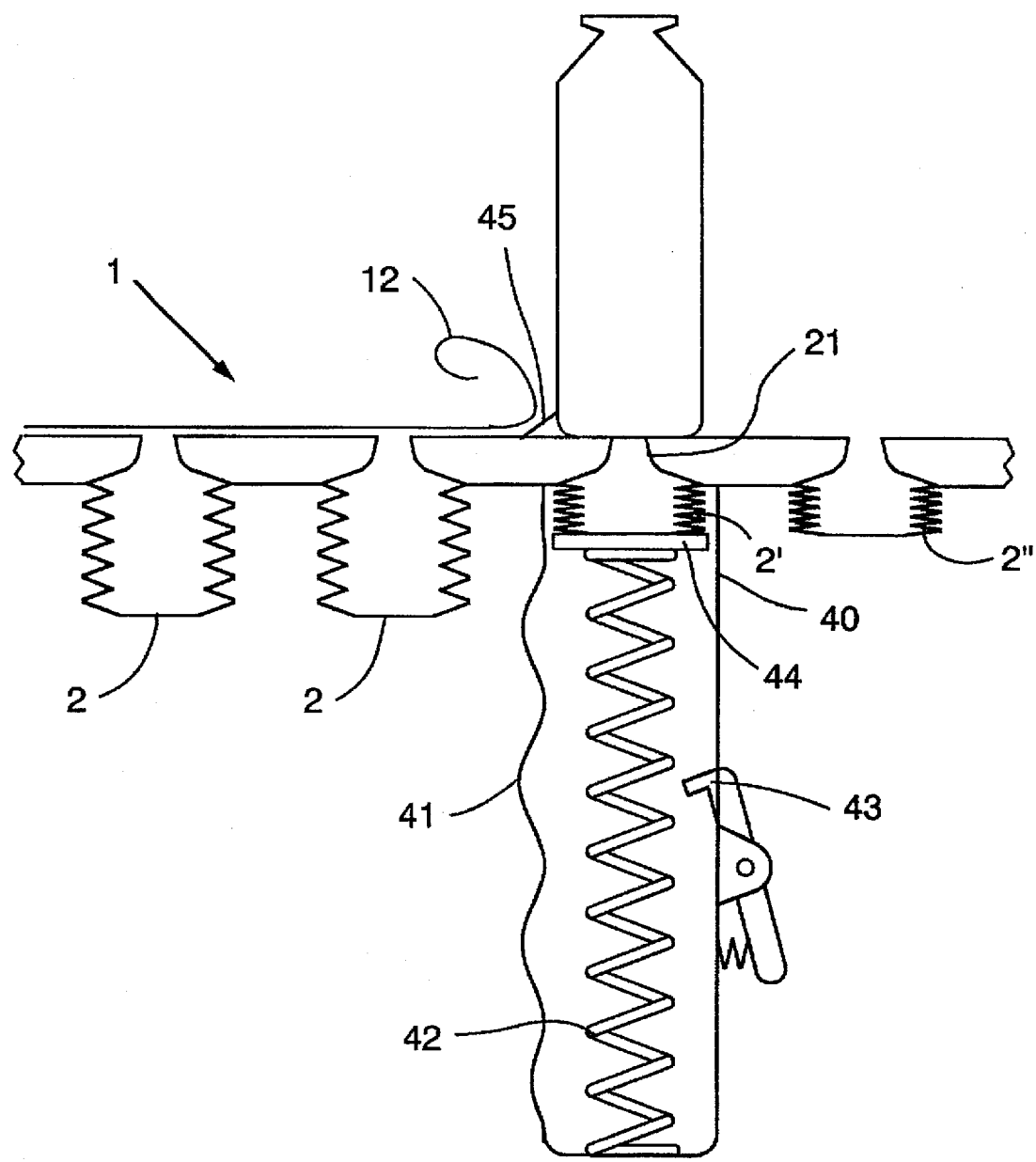
FIG. 5 is a cross-sectional plan view of a drug dispensing device of the invention.
Figure 6:
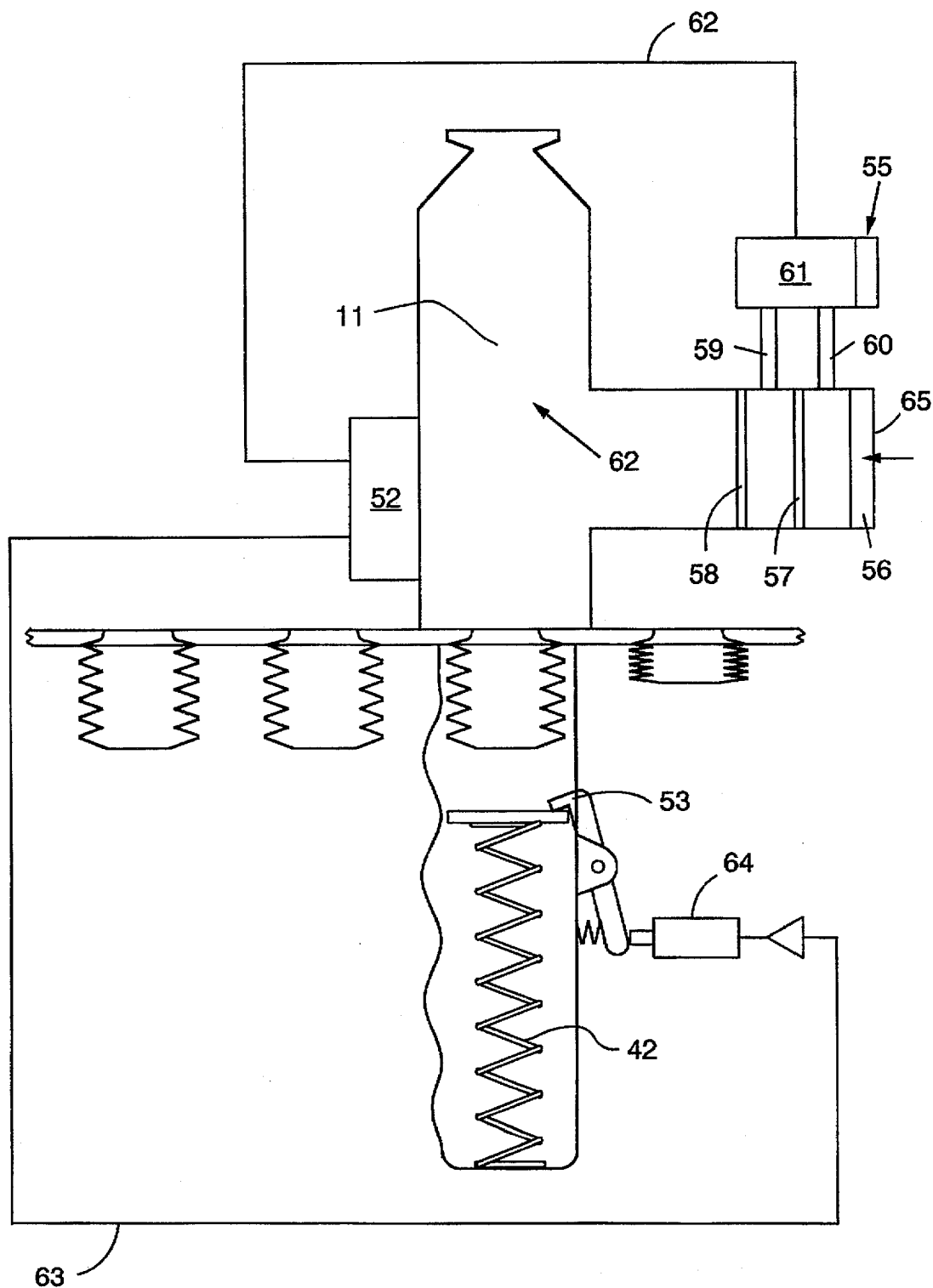
FIG. 6 is a cross-sectional plan view of another embodiment of a drug dispensing device of the invention.

Before referring to the specific embodiments of the delivery devices shown in FIGS. 5 and 6, an explanation will be provided regarding a general mechanism which can be used in connection with the method of intrapulmonary administration of a drug such as a respiratory drug. The drug delivery device is shown in FIGS. 5 and 6 could be further modified to include a vibrating means of the type as shown in connection with FIGS. 7 and 8. However, in order to provide for a clear explanation, the devices of FIGS. 5 and 6 will first be described without a description of the vibrating means shown in FIG. 7 and 8. This approach will provide a clearer description of more simple forms of the drug delivery devices as shown in FIGS. 5 and 6. Such a device is a hand-held, portable device which is comprised of (a) a device for holding a cellular array, (b) a mechanical mechanism for forcing the contents of a container (on the array) from an opening in the container and preferably (c) a means for analyzing the inspiratory flow of a patient and (d) a means for automatically releasing or firing the mechanical means after the inspiratory flow and/or volume reaches a threshold level. The device for holding the cellular array may be nothing more than a narrow opening created between two outwardly extending bars or may include additional components such as one or more wheels or rollers rotably mounted on the end(s) of such bars. The rollers may be spring mounted so as to provide constant pressure against the surface(s) of the cellular array. The device may also include a transport mechanism which may include providing drive power to the roller(s) so that when they are rotated, they move the cellular array from one container to the next. The power driving the roller(s) is programmed to rotate the rollers only enough to move the cellular array from one container to the next. In order to use the device, the device must be "loaded", i.e. connected to a cellular array which includes drug dosage units having liquid, flowable formulations of pharmaceutically active drug therein. The entire device is self-contained, light weight (less than 1 kg preferably less than 0.5 kg loaded) and portable.

The device preferably includes a mouth piece at the end of the flow path, and the patient inhales from the mouth piece which causes an inspiratory flow to be measured within the flow path. This inspiratory flow causes an air flow transducer to generate a signal. This signal is conveyed to a microprocessor which is able to convert, continuously, the signal from the transducer in the inspiratory flow path to a flow rate in liters per minute. The microprocessor can further integrate this continuous air flow rate signal into a representation of cumulative inspiratory volume. At an appropriate point in the inspiratory cycle, the microprocessor can send a signal to an actuation means. When the actuation means is signaled, it causes the mechanical means to force drug from a container on the cellular array into the inspiratory flow path of the device and ultimately into the patient's lungs. After being released, the drug and propellant will preferably pass through a nozzle prior to entering the inspiratory flow path of the device to aerosolize the formulation and thereafter the lungs of the patient.

It is important to note that the firing threshold of the device is preferably not based on a single criterion such as the rate of air flow through the device or a specific time after the patient begins inhalation. The firing threshold is based on an analysis of the patient's inspiratory flow profile. This means that the microprocessor controlling the device takes into consideration the instantaneous air flow rate as well as the cumulative inspiratory flow volume when it determines the optimal point in the patient's inspiratory cycle which would be most preferable in terms of reproducibly delivering the same amount of drug to the patient with each release of drug.

The device preferably includes a means for recording a characterization of the inspiratory flow profile for the patient which is possible by including a microprocessor in combination with a read/write memory means and a flow measurement transducer. By using such devices, it is possible to change the firing threshold at any time in response to an analysis of the patient's inspiratory flow profile, and it is also possible to record drug dosing events over time. In a particularly preferred embodiment the characterization of the inspiratory flow can be recorded onto a recording means on the cellular array.

FIG. 5 shows a cross-sectional view of a hand held, self-contained, portable, breath-actuated inhaler device of the present invention. The device is shown with a holder 40 having cylindrical side walls and a hand grip 41. The holder 40 is "loaded" in that it includes a cellular array 1. The array 1 includes a plurality of containers 2.

The embodiment shown in FIG. 5 is a simple version of the invention and is not the preferred embodiment. The device is manually actuated and loaded. More specifically, the spring 42 is compressed by the user until it is forced down below the actuation mechanism 43. When the user pushes the actuation mechanism 43 the spring 42 is released and the mechanical means in the form of a plate 44 is forced upward against a container such as the container 2' shown in a compressed state in FIG. 5. When the container 2' is compressed its contents is forced out through the nozzle 21 and aerosolized. A container 2" is shown to the right in a used state. Other containers 2 are shown to the left which are unused. A top cover sheet 12 has been peeled away from the top opening of the nozzle 21 by a peeling means 45. The embodiment of FIG. 5 would essentially provide the same results as a conventional metered dose inhaler. However, the device of FIG. 5 would not require the use of low boiling point propellants such as low boiling point fluorocarbons. Numerous additional features and advantages of the present invention can be obtained by utilizing a more preferred embodiment as is shown within FIG. 6 described below.

It is important to note that a variety of devices can be used in order to carry out the methodology (including the respiratory disease treatment methodology) of the present invention. However, the device must be capable of aerosolizing drug formulation in a container and preferably does such based on pre-programmed criteria which are readable by the microprocessor 52 as shown in FIG. 6. The details of the microprocessor and the details of other drug delivery devices which include a microprocessor and pressure transducer of the type used in connection with the present invention are described and disclosed within U.S. patent application Ser. No. 07/664,758, filed on Mar. 5, 1991 entitled "Delivery of Aerosol Medications for Inspiration" which application is incorporated in its entirety herein by reference, and it is specifically incorporated in order to describe and disclose the microprocessor and program technology used therewith. The pre-programmed information is contained within a nonvolatile memory which can be modified via an external device. In another embodiment, this pre-programmed information is contained within a "read only" memory which can be unplugged from the device and replaced with another memory unit containing different programming information. In yet another embodiment, microprocessor 52, containing read only memory which in turn contains the pre-programmed information, is plugged into the device. For each of these three embodiments, changing the programming of the memory device readable by microprocessor 52 will radically change the behavior of the device by causing microprocessor 52 to be programmed in a different manner.

Microprocessor 52 sends signals via electrical connection 63 to electrical actuation device 64 which actuates the means 43 which fires the mechanical means forcing drug formulation in a container to be aerosolized so that an amount of aerosolized drug is delivered into the inspiratory flow path. The device 64 can be a solenoid, motor, or any device for converting electrical to mechanical energy. Further, microprocessor 52 keeps a record of all drug dosing times and amounts using a read/write non-volatile memory which is in turn readable by an external device. Alternatively, the device records the information onto an electronic or magnetic strip (35 shown in FIG. 4) on the cellular array. The recorded information can be read later by the care-giver to determine the effectiveness of the treatment. In order to allow for ease of use, it is possible to form inspiratory flow path 11 into a mouth piece which can be specifically designed to fit the mouth of a particular patient using the device.

The electrical actuation means 64 is in electrical connection with the flow sensor 55 which is capable of measuring a flow rate of about 0 to about 800 liters per minute. The flow sensor 55 includes screens 56, 57 and 58 which are positioned approximately ¼" apart from each other. Tubes 59 and 60 open to the area between the screens 56, 57 and 58 with the tubes 59 and 60 being connected to a conventional differential pressure transducer 61. Another transducer designed to measure outflow through the opening 65 is also preferably included or the flow sensor 55 is designed so that the same components can measure inflow and outflow. When the user draws air through inspiratory flow path 62, air is passed through the screens 56, 57 and 58 and the air flow can be measured by the differential air pressure transducer 61. Alternatively, other means to measure pressure differential related to air flow, such as a conventional measuring device in the air way, may be used. The flow sensor 55 is in connection with the electrical actuation means 64 (via the connector 62 to the processor 52), and when a threshold value of air flow is reached (as determined by the processor 55), the electrical actuation means 64 fires the release of a mechanical means 43 releasing the piston 44 which forces the release of formulation from a container 2 so that a controlled amount of respiratory drug is delivered to the patient.

The device of FIG. 6 shows all of the components present within the single, hand-held, portable device, e.g. the microprocessor 52 and flow sensor 55 not part of the device of FIG. 5 are part of the device in FIG. 6. Like the device shown within FIG. 5, the device of FIG. 6 includes a holding means and mechanical means. However, unlike the device of FIG. 5, the device of FIG. 6 operates electronically, i.e. the actuation means is not directly released by the user. Like the device shown within FIG. 5, the patient inhales through inspiratory flow path 11 which can form a mouth piece. Air enters the device via the opening 65. The inhaling is carried out in order to obtain a metering event using the differential pressure transducer 61. Further, when the inspiratory flow meets a threshold of a pre-programmed criteria, the microprocessor 52 sends a signal to an actuator release electrical mechanism 64 which actuates the mechanical means 43, thereby releasing a spring 42 and plate 44 or equivalent thereof, forcing aerosolized formulation into the inspiratory flow path 11. Further details regarding microprocessors of FIG. 6 are described within co-pending U.S. patent application entitled "An Automatic Aerosol Medication Delivery System and Methods", filed on Jan. 29, 1993 as Ser. No. 08/002,507, which application is incorporated herein by reference in its entirety and specifically incorporated in order to describe and disclose flow measurements, the microprocessor and program technology used therewith.

Microprocessor 52 of FIG. 6 includes an external non-volatile read/write memory subsystem, peripheral devices to support this memory system, reset circuit, a clock oscillator, a data acquisition subsystem and an LCD annunciator subsystem. The discrete components are conventional parts which have input and output pins configured in a conventional manner with the connections being made in accordance with instructions provided by the device manufacturers. The microprocessor used in connection with the device of the invention is designed and programmed specifically so as to provide controlled and repeatable amounts of respiratory drug to a patient upon actuation. Adjustments can be made in the program so that when the patient's inspiratory flow profile is changed such is taken into consideration. This can be done by allowing the patient to inhale through the device as a test in order to measure air flow with preferred drug delivery points determined based on the results of several inhalations by each particular patient. This process can be readily repeated when the inspiratory flow profile is changed for whatever reason. When the patient's lung function has decreased the program will automatically back down in terms of the threshold levels required for release of drug. This "back down" function insures drug delivery to a patient in need but with impaired lung function. Determination of optimal drug delivery points in the inspiratory flow can be done at each dosing event, daily, weekly, or with the replacement of a new cellular array in the device.

The microprocessor of the present invention, along with its associated peripheral devices, can be programmed so as to prevent triggering the actuation mechanism 43 more than a given number of times within a given period of time. This feature makes it possible to prevent overdosing the patient. The overdose prevention feature can be particularly designed with each individual patient in mind or designed with particular groups of patients in mind. For example, the microprocessor can be programmed so as to prevent the release of more than approximately 200 µg of a given respiratory drug per day when the patient is normally dosed with approximately 100 µg of drug per day. The device can be designed to switch off this lock-out function so that drug can be delivered in an emergency situation.

The systems can also be designed so that only a given amount of a particular drug such as a respiratory drug is provided at a given dosing event. For example, the system can be designed so that only approximately 10 µg of respiratory drug is given in a given 15-minute period over which the patient will make approximately 10 inhalations with 1 µg of drug being delivered with each inhalation. By providing this feature, greater assurances are obtained with respect to delivering the respiratory drug gradually over time and thereby providing relief from the symptoms of respiratory disease without overdosing the patient.

The microprocessor of the invention can be connected to external devices permitting external information to be transferred into the microprocessor of the invention and stored within the non-volatile read/write memory available to the microprocessor. The microprocessor of the invention can then change its drug delivery behavior based on this information transferred from external devices. All of the features of the invention are provided in a portable, programmable, battery-powered, hand-held device for patient use which has a size which compares favorably with existing metered dose inhaler devices.

The microprocessor of the present invention is programmed so as to allow for monitoring and recording data from the inspiratory flow monitor without delivering drug. This is done in order to characterize the patient's inspiratory flow profile in a given number of monitoring events, which monitoring events preferably occur prior to dosing events. After carrying out a monitoring event, the preferred point within the inspiratory cycle for drug delivery can be calculated. This calculated point is a function of measured inspiratory flow rate as well as calculated cumulative inspiratory flow volume. This information is stored and used to allow activation of the electronic actuation means when the inhalation cycle is repeated during the dosing event.

The device described in FIGS. 5 and 6 can be modified to include a vibrating means of the type which is now to be described in connection with FIGS. 7 and 8. FIG. 7 shows a containers 70 having cylindrical walls and a bottom collapsible wall 71. The top portion of the container is covered by a polycarbonate membrane 72 and the membrane 72 has a cover film 73 positioned thereon. The container 70, shown in FIG. 7, is preferably loaded into a device as per either FIGS. 5 or 6 in a manner such that the cover film 73 is pealed back allowing complete access of the membrane 72 on the top of the container 70. At this point a piston such as the piston 75 is fired against the bottom wall 71 collapsing the container 70 and forcing the contents 86 therein outward through the plurality of pores in the polycarbonate membrane 72. This operation is essentially identical to the operation described in connection in FIGS. 5 and 6. However, the piston 75 includes a means for generating vibrations such as the vibrator 76 positioned within the piston 75. The vibrator 76 is electrically powered by electrical connections 77.

The vibrator 76 is designed so as to generate vibrations which affect the particle formation of formulation being forced out of the pores within the membrane 72. The frequency of the vibrations can be varied depending upon the size of the pores in the membrane 72 and the viscosity of the formulation present within the container 70. However, in general, the vibrations are within the range of about 1 kilohertz to about 1,000 kilohertz.

FIG. 8 shows another embodiment which includes a vibrator 76. However, the embodiment shown in FIG. 8 is different in that the container 80 is formed as an outwardly extending protuberance of the connecting means 81. This is different from the embodiment of FIG. 7 which shows a cellular array which would be substantially plainer on both surfaces and include the container 70 as an opening within the connecting means 74. In accordance with the embodiment of FIG. 8 a cylindrical holding means 82 is positioned around the container 80. Once in position the spring 42 is actuated in order to compress the container 80 and force the formulation contents through the pores of the polycarbonate membrane 72. In order to prevent the piston 75 from being forced ahead too quickly or being forced through the membrane 72, light springs 83 and 84 are provided as is an abutment 85 which extends annually from the base of the circumference of the piston 75.

Although the vibrator 76 is shown positioned within the piston 75, it should be noted that the vibrator can be positioned with the holding means 82 which would allow vibration of the container 80, its contents and the polycarbonate membrane 72. The precise positioning and type of vibrator used is not of particular importance. However, those skilled in the art will recognize that the vibrator must generate a vibration frequency within a certain range in order to obtain the desired particle size with respect to the container contents being forced through the openings on the polycarbonate membrane 72. The embodiments shown in FIGS. 7 and 8 are particularly preferred in that these embodiments allow the creation of a fine aerosolized mist without the need for any specially designed nozzle on either the container or the drug dispensing device. The polycarbonate membranes 72 shown having desired pore size and pore density can be purchased commercially. Further, they can be designed so that the pores are positioned only over the tops of the containers or can be designed so that pores are positioned everywhere. In that the membranes can be commercially purchased with the pores positioned throughout, such is a preferred form and would make it possible to produce the device without the need for precise positioning with respect to locating the pores over the tops of the container 70 or 80 in FIGS. 7 and 8 respectively.

The embodiments shown in FIGS. 7 and 8 do not show the microprocessor 52 shown in FIG. 6 or any of the components necessary in order to measure inspiratory flow. However, the most preferred form of the present invention would include such a microprocessor and mechanisms for measuring inspiratory flow. Thus, preferred embodiments would include a system such as shown within FIG. 6 as modified by the inclusion of the vibrator shown in FIGS. 7 and 8 and, further modified by the inclusion of the particular cellular array designs shown in either of FIGS. 7 or 8 which designs include the use of the polycarbonate membrane 72.

Figure 10:
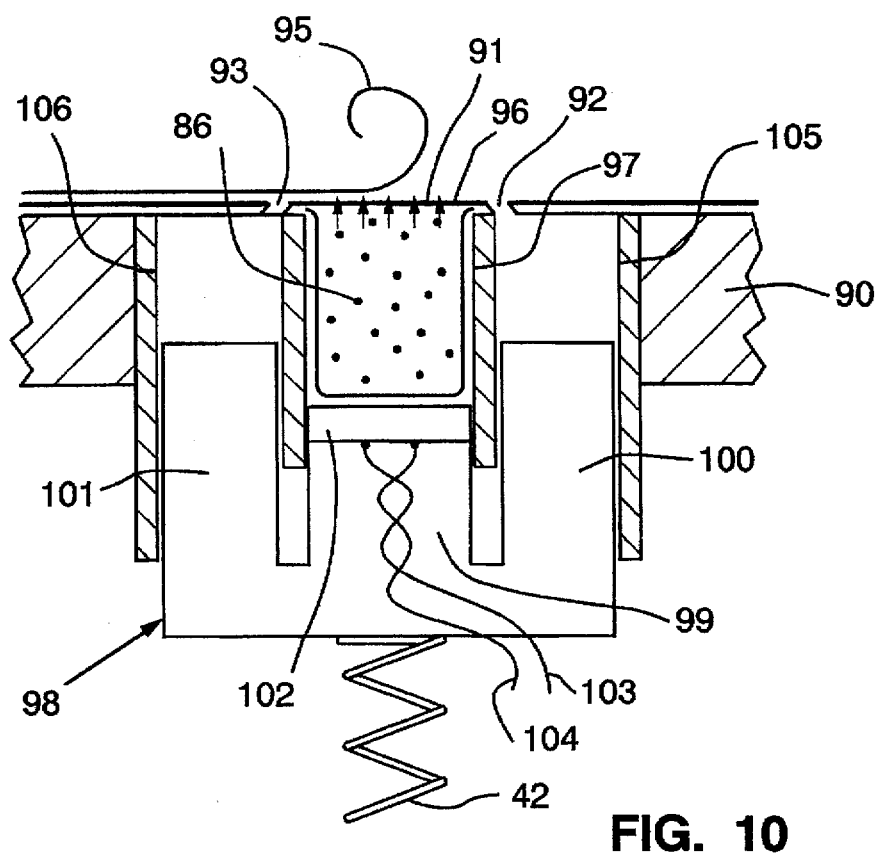
FIG. 10 is a cross-sectional view of a container of the cellular array of FIG. 9 shown in position above pistons of a dispensing device.

FIG. 10 is a cross-sectional view showing the cellular array 90 of FIG. 9 inserted within a drug dispensing device. The array 90 includes the openings 91, each of which are covered by a porous membrane 96. Further, each opening 91 is positioned in close proximity to an opening 92 on one side and 93 on the opposite side. Before dispensing drugs, all of the openings 91, 92, and 93 are covered by a cover sheet 95 which is shown being peeled back. When the cover sheet 95 is completely peeled back, the contents 86 of the container 97 may be dispersed outwardly through the membrane 96 covering the opening 91. This is done in a manner similar to the operation described above with respect to FIG. 7. However, in FIG. 10, the piston 98 is comprised of a main piston component 99 and additional piston components 100 and 101. The main piston component 99 includes a vibrating device 102 electrically connected by connectors 103 and 104. Like the device shown in FIG. 7, the piston 98 is forced upward by an expanding spring 42.

The main piston in 99 will force the contents 86 of the container 97 outward through the membrane 96. When forced outward through the porous openings of the membrane 96, the liquid will be in a stream form which stream is broken by the effect of the vibrator 102, thus allowing for the formation of small particles which create the desired aerosol. However, the particles of the aerosol immediately encounter frictional resistance from air molecules and can be slowed down quickly causing the particles to collide with one another and combine. In order to avoid this, the pistons 100 and 101 force air out of the containers 105 and 106, respectively. The air is forced out of the containers via the openings 92 and 93. It is preferable to have the containers 105 and 106 of a size which is larger than the container 97. The size of the containers can be adjusted depending upon parameters such as the particular liquid 86 in the containers and the size of the pores of the membrane 96. However, the general object to be obtained is to create an airflow from the openings 92 and 93 which aiding in preventing particle collisions. The air flow is generally equal to or greater than the flow rate of the particles being forced from the container 97. Creating such an air flow aids in preventing the collision of particles forced from the container 97.

The piston components 100 and 101 should each be designed so as to fit tightly against the walls of the container which they are positioned within. This may be accomplished with piston rings and/or similar devices which will make it possible to more efficiently force the contents of the containers 105 and 106 outward. Alternatively, the containers 105 and 106 may be sealed except at the top openings 92 and 93 so that the pistons collapse the containers.

Although the piston 98 has been shown as a three-component piston, all operated by a single force-providing mechanism (e.g. 42), the system can be designed so that the components 99, 100, and 101 are individual pistons with individuals force-providing mechanisms. Further, the embodiment shown provides openings 92 and 93 which are opened when the cover 95 is peeled back. However, these openings 92 and 93 could be covered by cover components which prevent compressed gas present within the containers 105 and 106 from escaping until additional pressure is provided by the pistons 100 and 101, at which point, the covers will rupture and allow the compressed gas to escape. Other configurations will, of course, be contemplated by those skilled in the art upon reading this disclosure. Components such as those shown can be modified and/or different components can be used to achieve a desired object of the invention which is to create an aerosol from the liquid 86 present in the container 97, which aerosol has a relatively narrow particle distribution and a relatively small particle size. In that FIG. 10 is a cross-sectional view, it may not be readily apparent that the piston components 99, 100, and 101 are rectangular in shape. However, their cross-sectional shape is rectangular to match the configurations shown in FIG. 9.

The instant invention is shown herein in what is considered to be the most practical and preferred embodiments. It is recognized, however, that departures may be made therefrom which are within the scope of the invention and that obvious modifications will occur to one skilled in the art upon reading this disclosure.

What is claimed is:

1. A hand-held, self-contained drug delivery system for intrapulmonary delivery of drugs, comprising:

a cellular array comprised of a plurality of interconnected individual containers with each container having a disposable membrane thereon wherein the membrane includes a plurality of pores therein which pores are provided in a pore density of about $1 \times 10^5$ to about $1 \times 10^8$ pores/cm$^2$ and which have a diameter in the range of about 0.5 to about 5 microns the container having therein a liquid formulation comprising a pharmaceutically active drug wherein each container includes a wall which is collapsible by the application of sufficient pressure to force the liquid formulation out of the container and form particles sufficiently small such that a patient can inhale the particles;

a transport mechanism for successively moving each individual container into a drug release position for release of the drug therefrom;

a mechanical mechanism for applying force to the collapsible wall of an individual container upon actuation;

a housing interconnecting the transport mechanism and mechanical mechanism, while allowing the cellular array to be moved so that successive containers on the cellular array are placed in the drug release position; and an instrument for measuring inspiratory flow and sending an electrical signal as an indication of the measurement; and a microprocessor programmed to receive, analyze and store the electrical signal of the instrument for measuring flow and upon receipt of a threshold signal value sending an actuation signal to the mechanical mechanism for applying force.

2. The drug delivery system of claim 1, further comprising:

a vibrating device for vibrating each membrane at frequency such that when formulation is forced from the pores the formulation is aerosolized.

3. The drug delivery system of claim 2 wherein the mechanical mechanism is in the form of a piston and the vibrating device is in the piston.

4. The drug delivery system of claim 1, wherein the membrane has a density in the range of 0.5 to 2.0 mg/cm$^2$ and a thickness in the range of about 2 to about 20 microns.

5. The drug delivery system of claim 4, wherein the membrane has a thickness in the range of 8 to 12 microns.

6. A hand-held, self-contained drug dispersing dosage unit for intrapulmonary delivery of drugs, comprising:

a first disposable container having a plurality of openings thereof with each opening having a diameter of about 0.5 micron to about 5 microns, a pharmaceutically active drug therein and an opening allowing inflow; and a second disposable container having at least one wall with a portion thereon designed to rupture upon the application of pressure which portion is positioned adjacent to the opening in the first container and at least one wall collapsible in a manner so as to increase the pressure of the contents in the second container in an amount sufficient to rupture said one wall portion.

7. The dosage unit of claim 6, wherein the pharmaceutically active drug is a respiratory drug.

8. The dosage unit of claim 6, wherein the respiratory drug is selected from the group consisting of a bronchodilator and a non-steroidal anti-inflammatory drug.

9. The dosage unit of claim 6, wherein the pharmaceutically active drug is a drug which has a systemic effect.

10. The dosage unit of claim 9, wherein the drug which has a systemic effect is a protein.

11. The dosage unit of claim 10, wherein the protein is DNAse.

12. The drug delivery system of claim 6, wherein the membrane has a density in the range of 0.5 to 2.0 mg/cm$^2$ and a thickness in the range of about 2 to about 20 microns.

13. The drug delivery system of claim 12, wherein the membrane has a thickness in the range of 8 to 12 microns.

* * * * *